United States Patent [19]

Alisch et al.

[11] Patent Number: 5,212,187

[45] Date of Patent: May 18, 1993

[54] PYRIDYL ALKYLAMINE COMPOUNDS WHICH ARE USEFUL AGAINST HISTAMINE $H_1$ AND $H_2$ RECEPTORS

[75] Inventors: Rudi A. Alisch; Frank R. Schulze; Armin Buschauer; Walter Schunack, all of Berlin, Fed. Rep. of Germany

[73] Assignee: Zyma SA, Nyon, Switzerland

[21] Appl. No.: 914,584

[22] Filed: Jul. 20, 1992

[30] Foreign Application Priority Data

Jul. 22, 1991 [CH] Switzerland .................. 2193/91

[51] Int. Cl.$^5$ ............... A61K 31/44; C07D 213/02
[52] U.S. Cl. .................... 514/342; 514/318; 514/336; 546/194; 546/283
[58] Field of Search ............. 546/280, 194, 283; 514/342, 318, 336

[56] References Cited

U.S. PATENT DOCUMENTS

| | | | |
|---|---|---|---|
| 4,492,711 | 1/1985 | Nisato et al. | 424/285 |
| 4,526,995 | 7/1985 | Nisato et al. | 549/494 |
| 4,837,316 | 6/1989 | Sekine et al. | 546/214 |
| 4,912,119 | 3/1990 | Buschauer et al. | 514/333 |

FOREIGN PATENT DOCUMENTS

| | | | |
|---|---|---|---|
| 0066987 | 5/1981 | European Pat. Off. | 546/280 |
| 0132366 | 7/1983 | European Pat. Off. | 548/123 |
| 0101379 | 2/1984 | European Pat. Off. | 549/494 |
| 0166355 | 6/1984 | European Pat. Off. | 544/126 |
| 0214823 | 3/1987 | European Pat. Off. | 546/214 |
| 0262448 | 4/1988 | European Pat. Off. | 514/333 |

OTHER PUBLICATIONS van der Stelt et al., Chem. Abstr., vol. 68, p. 4647 (1968) Abstract No. 48142d.

Primary Examiner—C. Warren Ivy
Assistant Examiner—Zinna N. Davis
Attorney, Agent, or Firm—Wenderoth, Lind & Ponack

[57] ABSTRACT

Arylalkylamine derivatives of the general formula

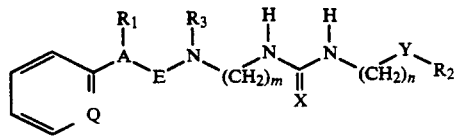

are described which, owing to their anatagonistic action against histamine $H_1$- and $H_2$-receptors, can be used for the prophylaxis and treatment of disorders in which histamine is involved. They are prepared in a manner known per se.

10 Claims, No Drawings

PYRIDYL ALKYLAMINE COMPOUNDS WHICH ARE USEFUL AGAINST HISTAMINE $H_1$ AND $H_2$ RECEPTORS

The invention relates to arylalkylamine derivatives which, owing to their antagonistic action against histamine $H_1$- and $H_2$-receptors, can be used for the prophylaxis and treatment of disorders in which histamine is involved.

A large number of active ingredients that are used in anaesthesia and surgery, as well as surgery per se, may cause a massive release of histamine from mast cells. The liberation of histamine and the subsequent activation of histamine $H_1$- and $H_2$-receptors may lead to a clinical picture of anaphylactic or anaphylactoid reaction in varying degrees of severity, from local erythema formation to systemic urticaria with serious decrease in blood pressure, cardiac arrythmia and potentially fatal bronchospasms.

The stimulation of histamine $H_1$-receptors is, inter alia, a cause of the contraction of smooth muscles, for example the bronchia, and of complex cardiovascular effects, for example the contraction or dilatation of vessels, an increase in the permeability of the venule endothelium with exudation and haemoconcentration, prolonging of the atrioventricular transmission of stimuli to the extent of an AV block. The activation of the $H_2$-receptors results, inter alia, in an increase in the heart rate, promotion or induction of tachycardiac cardiac irregularity and increased vasodilation. In addition, $H_2$-receptors of the parietal cells of the gastric mucosa bring about an increase in acid secretion with the risk of pulmonary damage resulting from acid aspiration and the formation of stress ulcers.

A significant reduction in those reactions can be achieved by the combined administration of a histamine $H_1$-receptor-antagonist and a histamine $H_2$-receptor-antagonist before surgery (Lorenz, W.; Doenicke, A. (1985), "$H_1$- and $H_2$-blockade: A prophylactic principle in anaesthesia and surgery against histamine-release responses of any degree of severity", N. Engl. Reg. Allergy Proc. 6, 37–57. Tryba, M.; Zevounou, F.; Zenz, M. (1986), "Prevention of histamine-induced cardiovascular reactions during the induction of anaesthesia following premedication with $H_1$-+$H_2$-antagonists i.m.", Br. J. Anaesth. 58, 478–482).

Owing to its above-mentioned effects on $H_1$- and $H_2$-receptors, histamine is also involved in various disorders, such as inflammatory skin disorders; pruritus (itching) of various origins, for example pruritus induced by solar radiation, atopic dermatitis and allergic dermatological disorders in general; urticaria, allergies, allergic asthma; rhinitis and allergic disorders of the respiratory organs in general; conjunctivitis and allergic opthalmic disorders in general; and mastocytosis.

The problem underlying the invention is therefore to provide compounds that are suitable for inhibiting the effects of histamine on both the $H_1$- and the $H_2$-receptors, and that are therefore suitable, for example, for treating the above-mentioned histamine-induced disorders.

The invention relates to arylalkylamine derivatives of the general formula I

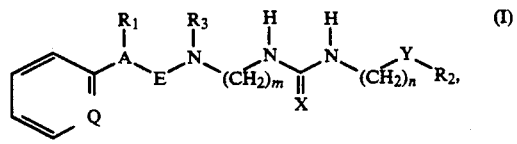

wherein $R_1$ is a substituted or unsubstituted aryl, heteroaryl, aryl-$C_1$-$C_3$alkyl or heteroaryl-$C_1$-$C_3$alkyl group, a hydrogen atom or a $C_1$-$C_3$alkyl group, A is a nitrogen atom or a CH group, E is the grouping —$(CH_2)_p$—, —O—$(CH_2)_p$—, —S—$(CH_2)_p$— or

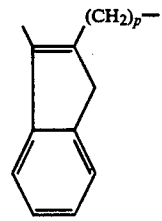

wherein p may be 2, 3 or 4, Q is a nitrogen atom or a CH group, $R_2$ is an unsubstituted or basically substituted aryl, heteroaryl, aryl-$C_1$-$C_3$alkyl or heteroaryl-$C_1$-$C_3$alkyl group, $R_3$ is a hydrogen atom or a $C_1$-$C_3$alkyl group, preferably a methyl group, X is an oxygen atom, a sulfur atom, the grouping N—CN or CH—$NO_2$, m may be 2, 3, 4, 5, 6, 7 or 8 and n may be 1, 2, 3 or 4 and Y is a sulfur atom, an oxygen atom or a methylene group, and to pharmaceutically acceptable salts thereof, also to processes for the preparation of those compounds, to pharmaceutical compositions comprising those compounds and to the use of those compounds for the therapeutic treatment of the human or animal body or for the preparation of pharmaceutical compositions.

$C_1$-$C_3$alkyl is, for example, methyl. Halogen is, for example, fluorine, chlorine, bromine or iodine, preferably fluorine or chlorine. Phenyl-$C_1$-$C_3$alkyl is, for example, benzyl.

The radical $R_2$ is preferably piperidino-$C_1$-$C_3$alkylphenyl, guanidino-thiazolyl-$C_1$-$C_3$alkyl, $C_1$-$C_3$alkyl-imidazolyl-$C_1$-$C_3$alkyl or (N,N-di-$C_1$-$C_3$alkylamino-$C_1$-$C_3$alkyl)-furanyl-$C_1$-$C_3$alkyl.

The compounds of formula I according to the invention are distinguished by a novel overall pharmacological activity that has not been described hitherto. The novel structural class according to the invention exhibits both a histamine $H_1$-antagonistic component of action and a histamine $H_2$-antagonistic component of action. The following pharmacological results demonstrate this. Suitable for differentiating the two types of action are, for example, in vitro tests on isolated spontaneously beating guinea pig right atrium ($H_2$) and on isolated guinea pig ileum ($H_1$) (Black, J. W.; Duncan, W. A. M.; Durant, G. J., Ganellin, C. R.; Parsons, M. E. (1972), "Definition and Antagonism of Histamine $H_2$-receptors", Nature 236, 385–390). The concentration/action curves for determining the pharmacological parameters ($-\log K_B$) are recorded using a cumulative technique according to van Rossum, J. M. (1963), "Cumulative Dose-Response Curves. II. Technique for the Making of Dose-Response Curves in Isolated Organs and the Evaluation of Drug Parameters", Arch. Int. Pharmacodyn. Ther. 143, 299–307.

| Pharmacological data (determined from isolated guinea pig ileum and atrium, respectively) | | |
| --- | --- | --- |
| Compounds | $H_1$-antagonism ileum- log $K_B$ | $H_2$-antagonism atrium- log $K_B$ |
| Example 1 | 7.20 | 5.64 |
| Example 9 | 7.93 | 6.30 |
| Example 10 | 8.19 | 5.83 |
| Example 17 | 8.30 | 6.78 |
| Example 18 | 8.43 | 6.90 |
| Example 20 | 8.38 | 7.51 |
| Example 23 | 8.30 | 7.90 |
| Example 30 | 8.21 | 6.68 |
| Example 35 | 7.86 | 7.40 |
| Example 36 | 8.27 | 7.57 |
| Example 37 | 8.13 | 6.91 |
| Example 48 | 7.70 | 7.22 |
| Example 50 | 8.15 | 5.19 |
| Example 55 | 8.14 | 6.43 |
| Example 60 | 8.06 | 6.41 |
| Example 66 | 7.95 | 6.74 |
| Example 70 | 8.02 | 6.87 |
| Example 72 | 7.75 | 7.35 |
| Example 75 | 7.91 | 6.91 |
| Example 79 | 8.61 | 6.61 |
| Example 84 | 8.44 | 6.52 |
| Example 85 | 8.15 | 7.02 |
| Example 88 | 8.74 | 6.66 |
| Example 89 | 8.76 | 6.76 |
| Example 94 | 8.80 | 6.85 |
| Example 96 | 8.51 | 8.28 |
| Example 103 | 7.61 | 5.92 |
| Example 104 | 7.97 | 5.87 |
| Example 105 | 7.44 | 7.54 |

Preference is given to the arylalkylamine derivatives of formula I wherein $R_1$ is phenyl, furyl, thienyl, phenyl-$C_1$-$C_3$alkyl or (furyl, thienyl or pyridyl)-$C_1$-$C_3$alkyl, the phenyl ring and the heteroaryl ring in each case being unsubstituted or mono- or di-substituted by halogen, $C_1$-$C_3$alkyl and/or by $C_1$-$C_3$alkoxy, or $R_1$ is hydrogen or $C_1$-$C_3$alkyl, A is a nitrogen atom or a CH group, E is the grouping —$(CH_2)_p$—, —O—$(CH_2)_p$—, —S—$(CH_2)_p$— or

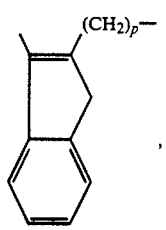

wherein p is 2, 3 or 4, Q is a nitrogen atom or a CH group, $R_2$ is piperidino-$C_1$-$C_3$alkyl-phenyl, guanidino-thiazolyl-$C_1$-$C_3$alkyl, $C_1$-$C_3$alkyl-imidazolyl-$C_1$-$C_3$alkyl or (N,N-di-$C_1$-$C_3$alkylamino-$C_1$-$C_3$alkyl)-furanyl-$C_1$-$C_3$alkyl, $R_3$ is hydrogen or $C_1$-$C_3$alkyl, X is an oxygen atom, a sulfur atom, the grouping N-CN or CH—$NO_2$, m is 2, 3, 4, 5, 6, 7 or 8 and n is 1, 2, 3 or 4, and Y is a sulfur atom, an oxygen atom or a methylene group, and to the stereoisomeric forms, the hydrates and the physiologically acceptable salts thereof.

In a preferred group of compounds of formula I according to the invention, $R_1$ is a phenyl ring that is unsubstituted or mono- or di-substituted, preferably monosubstituted, by halogen atoms, such as fluorine, chlorine or bromine atoms, preferably chlorine atoms, or by $C_1$-$C_3$alkyl groups, preferably methyl or ethyl groups, or by $C_1$-$C_3$alkoxy groups, such as methoxy or ethoxy groups, or a heteroaryl ring, such as a furyl or a thienyl ring, preferably a phenyl ring. Where the phenyl ring denoted by $R_1$ is monosubstituted, the substituent is preferably bonded in the para-position, a para-chlorine substitution being preferred. In the case of disubstitution, 3,4-, 3,5- and 2,4-disubstitution, especially 3,4-disubstitution, are preferred. A is a CH group or a nitrogen atom, Q is a nitrogen atom or a CH group, E, $R_2$, $R_3$, X, Y, m, n and p are as defined above.

In a further preferred group of compounds of formula I according to the invention, $R_1$ is a benzyl group or a heteroarylmethyl group, such as a furylmethyl, thienylmethyl or pyridylmethyl group, each of which is unsubstituted or mono- or di-substituted, preferably monosubstituted, by halogen atoms, such as fluorine, chlorine or bromine atoms, preferably fluorine or chlorine atoms, or by $C_1$-$C_3$alkyl groups, preferably methyl or ethyl groups, or by $C_1$-$C_3$alkoxy groups, such as methoxy or ethoxy groups, preferably methoxy groups, a benzyl group being preferred. Where the benzyl group denoted by $R_1$ is monosubstituted, the substituent is preferably bonded in the para-position, a para-fluorine or para-methoxy substitution being preferred. In the case of disubstitution, 3,4-, 3,5- and 2,4-disubstitution, especially 3,4-disubstitution, are preferred. Q is a nitrogen atom, A is a nitrogen atom and E is the grouping —$CH_2$—$CH_2$—. $R_2$, $R_3$, X, Y, m, n and p are as defined above.

Special preference is given to the arylalkylamine derivatives of formula I wherein $R_1$ is phenyl or phenyl-$C_1$-$C_3$alkyl, wherein the phenyl ring in each case is unsubstituted or substituted by halogen, $C_1$-$C_3$alkyl or by $C_1$-$C_3$alkoxy, or is hydrogen or $C_1$-$C_3$alkyl, A is a nitrogen atom or a CH group, E is the grouping —$(CH_2)_p$—, —O—$(CH_2)_p$—, —S—$(CH_2)_p$— or

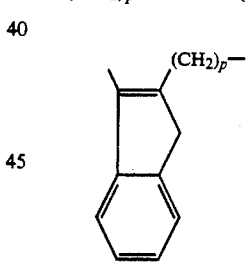

wherein p is 2 or 3, Q is a nitrogen atom or a CH group, $R_2$ is piperidino-$C_1$-$C_3$alkyl-phenyl, guanidino-thiazolyl-$C_1$-$C_3$alkyl, $C_1$-$C_3$alkyl-imidazolyl-$C_1$-$C_3$alkyl or (N,N-di-$C_1$-$C_3$alkylamino-$C_1$-$C_3$alkyl)-furanyl-$C_1$-$C_3$alkyl, $R_3$ is hydrogen or $C_1$-$C_3$alkyl, X is an oxygen atom, a sulfur atom, the grouping N—CN or CH—$NO_2$, m may be 2, 3, 4, 5, 6, 7 or 8 and n may be 1, 2, 3 or 4, and Y is a sulfur atom or an oxygen atom, and to the stereoisomeric forms, the hydrates and the physiologically acceptable salts thereof.

Very special preference is given to the arylalkylamine derivatives of formula I wherein $R_1$ is phenyl that is unsubstituted or substituted by halogen or by $C_1$-$C_3$alkyl, phenyl-$C_1$-$C_3$alkyl substituted in the phenyl ring by halogen or by $C_1$-$C_3$alkoxy, or is $C_1$-$C_3$alkyl, A is a nitrogen atom or a CH group, E is the grouping —$(CH_2)_p$—, —O—$(CH_2)_p$—, —S—$(CH_2)_p$— or

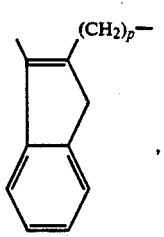

wherein p is 2, Q is a nitrogen atom or a CH group, $R_2$ is 3-piperidinomethyl-phenyl, 2-guanidino-thiazol-4-ylmethyl, 5-methyl-imidazol-4-ylmethyl or 5-(N,N-dimethylaminomethyl)-furan-2-ylmethyl, $R_3$ is $C_1$–$C_3$alkyl, X is an oxygen atom, a sulfur atom, the grouping N—CN or CH—$NO_2$, m may be 2, 3, 4, 5, 6, 7 or 8 and n may be 2, 3 or 4, and Y is a sulfur atom or an oxygen atom, and to the stereoisomeric forms, the hydrates and the physiologically acceptable salts thereof.

In a further preferred group of compounds of formula I according to the invention, $R_1$ is a hydrogen atom or a $C_1$–$C_3$alkyl group, preferably a methyl group, A is a CH group, Q is a nitrogen atom and E is the grouping

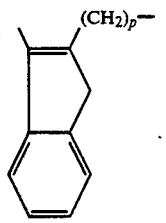

$R_2$, $R_3$, X, Y, m, n and p are as defined above.

In a preferred group of compounds of formula I according to the invention, $R_2$ is the grouping 5-methylimidazol-4-ylmethyl and $R_1$, $R_3$, A, E, Q, X, Y, m, n and p are as defined above.

In a further preferred group of compounds of formula I according to the invention, $R_2$ is the grouping

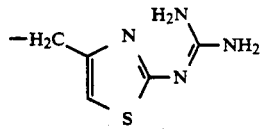

(=2-guanidino-thiazol-4-ylmethyl) and $R_1$, $R_3$, A, E, Q, X, Y, m, n and p are as defined above.

In a further preferred group of compounds of formula I according to the invention, $R_2$ is the grouping 5(N,N-dimethylaminomethyl)-furan-2-ylmethyl and $R_1$, $R_3$, A, E, Q, X, Y, m, n and p are as defined above.

In a further preferred group of compounds of formula I according to the invention, $R_2$ is the grouping 3-piperidinomethyl-phenyl and $R_1$, $R_3$, A, E, Q, X, Y, m, n and p are as defined above.

The invention also relates to all stereoisomeric forms and hydrates of the above-described compounds of the general formula I.

The invention relates especially to the specific compounds described in the Examples and to salts, especially pharmaceutically acceptable salts, thereof.

The compounds according to the invention can be prepared in a manner known per se, for example as follows:

a) for the preparation of a compound of formula I wherein X is an oxygen atom or a sulfur atom, or the grouping N—CN or CH—$NO_2$, (a1) a compound of formula II

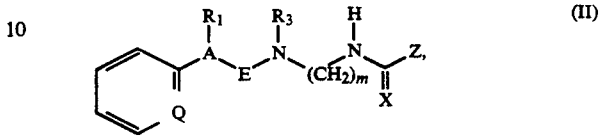

wherein $R_1$, $R_3$, A, E, Q and m are as defined above and Z is a methylthio, a mercapto or a phenoxy group, is reacted with a compound of the general formula III

wherein $R_2$, Y and n are as defined above, preferably in equimolar amounts in a polar solvent, such as an alcohol, for example methanol, ethanol or isopropyl alcohol, or in acetonitrile, dimethyl sulfoxide, dimethylformamide or pyridine, preferably acetonitrile, for example at room temperature or at the reflux temperature of the solvent in question, or (a2) a compound of formula IV

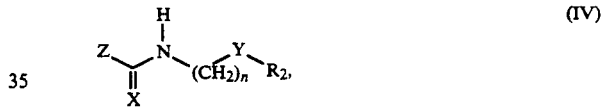

wherein $R_2$, Y and n are as defined above and Z is a methylthio, a mercapto or a phenoxy group, is reacted, preferably in equimolar amounts, with a compound of the general formula V

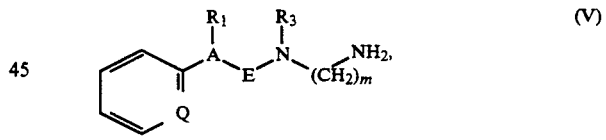

wherein $R_1$, $R_3$, A, E, Q and m are as defined in claim 1, preferably in a polar solvent as mentioned above, or b) for the preparation of a compound of formula I wherein X is an oxygen atom or a sulfur atom, (b1) a compound of formula VI

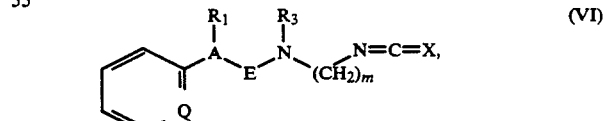

wherein $R_1$, $R_3$, A, E, Q and m are as defined above, is reacted, preferably in equimolar amounts, with a compound of formula III wherein $R_2$, Y and n are as defined above, preferably in an inert solvent, for example dimethylformamide or an ether, especially tetrahydrofuran, for example at room temperature or at the reflux temperature of the solvent in question, or (b2) a compound of formula VII

wherein $R_2$, Y and n are as defined above, is reacted, preferably in equimolar amounts, with a compound of formula V

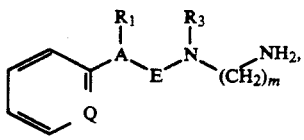

wherein $R_1$, $R_3$, A, E, Q and m are as defined above, preferably in an inert solvent as mentioned above, for example dimethylformamide or an ether, especially tetrahydrofuran, for example at room temperature or at the reflux temperature of the solvent in question;

and, if desired, a resulting compound of formula I is converted into a different compound of formula I, and/or, if desired, a resulting salt is converted into the free compound or into a different salt, and/or, if desired, a resulting free compound of formula I having salt-forming properties is converted into a salt, especially a physiologically acceptable salt.

Where appropriate, the compounds obtained in accordance with process a) or b) are chromatographed in a manner known per se and/or purified by a different method, for example by recrystallisation.

In addition to the stereoisomeric compounds and the hydrates of the compounds of the general formula I, the invention relates also to the physiologically acceptable salts of those compounds. Those salts may be formed, for example, with mineral acids, such as hydrochloric, hydrobromic or hydriodic acid, phosphoric acid, metaphosphoric acid, nitric acid or sulfuric acid, or with organic acids, such as formic acid, acetic acid, propionic acid, phenylacetic acid, tartaric acid, citric acid, fumaric acid, methanesulfonic acid or embonic acid.

Free compounds of formula I having salt-forming properties that are obtainable according to the process can be converted into their salts in a manner known per se, compounds having basic properties for example by treatment with acids or suitable derivatives thereof.

In view of the close relationship between the compounds of formula I in free form and in the form of their salts, hereinbefore and hereinafter any reference to the free compounds or their salts should be understood as including the corresponding salts or free compounds, as appropriate and expedient.

The reactions indicated above can be carried out under reaction conditions known per se, in the absence or, customarily, in the presence of solvents or diluents, preferably those that are inert towards the reagents used and are solvents thereof, in the absence or presence of catalysts, condensation agents or neutralising agents and, depending on the nature of the reaction and/or the reactants, at reduced, normal or elevated temperature, for example at a temperature in the range of from approximately $-70°$ C. to approximately $190°$ C., preferably from approximately $-20°$ C. to approximately $150°$ C., for example at the boiling point of the solvent used, under atmospheric pressure or in a closed vessel, where appropriate under pressure, and/or in an inert atmosphere, for example under a nitrogen atmosphere.

The starting materials used in the process of the present invention are preferably those which result in the compounds described at the beginning as being especially valuable.

The invention relates also to those forms of the process in which a compound obtainable as intermediate at any stage of the process is used as starting material and the remaining steps are carried out, or in which a starting material is formed under the reaction conditions or is used in the form of a derivative, for example a salt, thereof.

For the purpose of administration, the compounds according to the invention can be formulated in any desired manner. The invention therefore relates also to pharmaceutical compositions that comprise at least one compound according to the invention for use in human or veterinary medicine. Such medicaments can be prepared using one or more pharmaceutical carriers or diluents.

The compounds according to the invention can therefore be formulated, for example, for oral, buccal, topical, parenteral or rectal administration, oral administration being preferred.

For buccal administration the medicament may be in the form of, for example, tablets or wafers that have been formulated in conventional manner.

The compounds according to the invention can be formulated for parenteral administration, for example by bolus injection or by continuous infusion. Injection formulations may be, for example, in unit dose forms in the form of ampoules, or in repeat dose containers with added preservative.

The medicaments may also be in the form of, for example, suspensions, solutions or emulsions in oily or aqueous carriers, and they may comprise formulation excipients, such as suspension, stabilising and/or dispersing agents.

Alternatively, the active ingredient may also be in powder form intended for reconstitution with a suitable carrier, for example sterile, pyrogen-free water, before use.

The compounds according to the invention may be formulated, for example, also as rectal preparations, for example suppositories or retention enemas, which comprise, for example, suppository bases, such as cocoa butter or other glycerides.

For topical administration the compounds according to the invention may be formulated as, for example, ointments, creams, gels, lotions, powders or sprays.

For oral administration to a warm-blooded animal weighing approximately 70 kg, a suitable daily dose of compounds according to the invention is from 5 mg to 1 g, preferably from 5 to 250 mg, depending on the condition of the patient, divided into, for example, from 1 to 4 single doses. In individual cases it may be necessary to depart from the mentioned amounts, according to the individual response to the active ingredient or to the way in which it is formulated and to the time or frequency of administration. For example, there are cases in which it is possible to use less than the above-mentioned minimum amount, while in other cases the upper limit mentioned has to be exceeded.

The Examples that follow illustrate the present invention; "furfuryl" denotes "furan-2-ylmethyl".

EXAMPLE 1

N-[2-[N-[3-(4-chlorophenyl)-3-(2-pyridyl)propyl]-N-methylamino]ethyl]-N'-cyano-N''-[4-[3-(piperidinomethyl)phenoxy]butyl]guanidine A mixture of 0.8 g (2.6 mmol) of N-[3-(4-chlorophenyl)-3-(2-pyridyl)propyl]-N-methyl1,2-ethanediamine (A) and 0.8 g (2 mmol) of N-cyano-O-phenyl-N'-[4-[3-(piperidinomethyl)phenoxy]butyl]isourea (B) is heated under reflux for 12 hours in 20 ml of absolute acetonitrile. The batch is then freed of solvent in vacuo and the reaction product is isolated by means of preparative thick-layer chromatography (silica gel 60 PF254; ethyl acetate/methanol 95+5, ammonia atmosphere). The title compound is obtained in the form of a viscous oil; MS (+FAB method): m/z (rel. int. [%])=616 ([M+H]+, 9), 230 (100); IR (KBr): 2163 cm$^{-1}$ (C≡N). For analytical purposes a sample is converted into the O,O'-ditoluoyltartaric acid salt and recrystallised from ether/isopropanol; m.p.: from 135° C. with decomposition.

The starting materials are prepared as follows:

(A) A solution of 3-(4-chlorophenyl)-3-(2-pyridyl)-propaneamine [A. Buschauer, Arch. Pharm. (Weinheim) 322, 165-171 (1989)] (0.15 mol) in 100 ml of ether is provided with an underlayer of 100 ml of 10% NaOH and stirred vigorously while cooling with ice. Chloroformic acid ethyl ester is slowly added dropwise until no further precipitation occurs at the drip point. The organic phase is washed neutral with water, dried over Na$_2$SO$_4$, concentrated by evaporation in vacuo and dried intensively by means of relatively lengthy evacuation in an oil-pump vacuum. The resulting oil is sufficiently pure for further reaction. 0.12 mol of the reaction product is dissolved in 100 ml of absolute THF and the solution is added dropwise to a stirred and ice-cooled suspension of 9.4 g (0.24 mol) of LiAlH$_4$ in 150 ml of THF and the batch is heated under reflux for a further two hours. After cooling and the addition of water-saturated ether, approximately 10 ml of 10% NaOH are added to the batch, which is then stirred overnight. The precipitate is filtered off with suction and the clear filtrate is concentrated by evaporation in vacuo. The crude product, 3-(4-chlorophenyl)-3-(2-pyridyl)-N-methyl-1-propanamine [analogous to A. Buschauer, J. Med. Chem. 32, 1963 (1989)], is purified by column chromatography (ethyl acetate/ammoniacal methanol 99+1) and, in a batch size of 10-30 mmol, is then stirred for 2 hours at 60° C. with an equivalent amount of chloroacetonitrile, a spatula tip of potassium iodide and twice the molar excess of Na$_2$CO$_3$ in 20 ml of a mixture of equal parts of acetonitrile and DMF. When the reaction is complete (TLC monitoring, FM VI), 20 ml of water are added to the batch, which is extracted several times with toluene. The combined organic extracts are washed with water, dried over Na$_2$SO$_4$ and decolorised for column chromatography (CC) using a small amount of silica gel. Concentration by evaporation in vacuo yields the reaction product, 2-[N-[3-(4-chlorophenyl)-3-(2-pyridyl)propyl]-N-methylamino]acetonitrile of adequate purity in a yield of approximately 80%. The nitrile thus produced is dissolved in ether, added dropwise to an ice-cooled stirred suspension of LiAlH$_4$ (1.5 equivalents) in absolute ether (total volume approx. 50 ml) and left for 2 hours at room temperature. When reaction of the educt is complete, water-saturated ether and 2-3 ml of 10% NaOH are added to the batch, which is stirred at room temperature overnight. After removal of the inorganic phases by suction-filtration, the filtrate is concentrated by evaporation in vacuo and the resulting amine, if sufficiently pure, is reacted further or is isolated by means of preparative thick-layer chromatography.

(B) 4.6 g (0.2 mol) of sodium are dissolved in anhydrous ethanol and 38.24 g (0.2 mol) of 3-piperidinomethylphenol [DE-A-2 917 026, Glaxo] are added thereto. After the dropwise addition of 20.71 g (0.2 mol) of 4-chlorobutyronitrile in ethanol, the batch is heated under reflux overnight with the exclusion of moisture. It is then allowed to cool, is filtered, and concentrated to dryness in vacuo. The resulting oil is taken up in ether and washed with 10% NaOH and water. Drying over Na$_2$SO$_4$ and concentrating yield 35.5 g (0.14 mol) of 4-(3-piperidinomethylphenoxy)butyronitrile in the form of an oil that can be used in the subsequent reaction without further purification. While cooling with ice and stirring, 59.9 mmol of 4-(3-piperidinomethylphenoxy)butyronitrile are introduced slowly into a suspension of 2.98 g (78.4 mmol) of LiAlH$_4$ in 140 ml of anhydrous ether. After stirring for 40 min at room temperature the batch is hydrolysed, while cooling with ice, with 10 ml of water-saturated ether and 7 ml of 10% NaOH. Stirring is continued for 30 min, and then the batch is suction-filtered and the precipitate is washed several times with ether. The filtrate is washed with water, dried over Na$_2$SO$_4$, filtered and concentrated to dryness in vacuo to yield 4-(3-piperidinomethylphenoxy)butaneamine in the form of a low-viscosity brown oil that can be used in the subsequent reaction without further purification. The equimolar amount of 4-(3-piperidinomethylphenoxy)butaneamine is added while stirring to a suspension of N-cyanodiphenylimidocarbonate in 100 ml of diethyl ether. After stirring for approx. 15 min, the product, N-cyano-O-phenyl-N'-[4-(3-piperidinomethylphenoxy)butyl]isourea, precipitates copiously, or it crystallises when the solution is concentrated. The product is suction-filtered, washed with diethyl ether and dried.

EXAMPLE 2

N-[5-[N-[3-(4-chlorophenyl)-3-(2-pyridyl)propyl]-N-methylamino]pentyl]-N'-cyano-N''-[3-[3-(piperidinomethyl)phenoxy]propyl]guanidine Preparation is effected analogously to Example 1, using 1.09 g (3.15 mmol) of N-[3-(4-chlorophenyl)-3-(2-pyridyl)propyl]-N-methyl-1,5-pentanediamine and 1.23 g (3.1 mmol) of N-cyano-O-phenyl-N'-[3-[3-(piperidinomethyl)phenoxy]propyl]isourea as starting materials. Working up by chromatography analogously to Example 1 yields the purified title compound in the form of a viscous oil; IR (KBr): 2163 cm$^{-1}$ (C≡N).

EXAMPLE 3

N-[4-[N-[3-(4-chlorophenyl)-3-(2-pyridyl)propyl]-N-methylamino]butyl]-N'-cyano-N''-[3-[3-(piperidinomethyl)phenoxy]propyl]guanidine Preparation is effected analogously to Example 1, using 0.99 g (3 mmol) of N-[3-(4-chlorophenyl)-3-(2-pyridyl)propyl]-N-methyl-1,4-butanediamine and 1.17 g (3 mmol) of N-cyano-O-phenyl-N'-[3-[3-(piperidinomethyl)phenoxy]propyl]isourea as starting materials. Working up by chromatography (eluant: methylene chloride/methanol 98+2) analogously to Example 1 yields the purified title compound in the form of a viscous oil; MS (+FAB method): m/z (rel. int.[%])=630 ([M+H]+, 7), 230 (100); IR (KBr): 2164 cm$^{-1}$ (C≡N).

EXAMPLE 4

N-[3-[N-[3-(4-chlorophenyl)-3-(2-pyridyl)propyl]-N-methylamino]-propyl]-N'-cyano-N''-[3-[3-(piperidinomethyl)phenoxy]propyl]guanidine Preparation is effected analogously to Example 1, using 0.5 g (1.57 mmol) of N-[3-(4-chlorophenyl)-3-(2-pyridyl)propyl]-N-methyl-1,3-propanediamine and 0.6 g (1.5 mmol) of N-cyano-O-phenyl-N'-[3-[3-(piperidinomethyl)phenoxy]propyl]isourea as starting materials. Working up by chromatography (eluant: ethyl acetate) analogously to Example 1 yields the purified title compound in the form of a viscous oil; MS (+FAB method): m/z (rel. int.[%])=616 ([M+H]+, 1), 230 (100).

EXAMPLE 5

N-[2-[N-[3-(4-chlorophenyl)-3-(2-pyridyl)propyl]-N-methylamino]ethyl]-N'-cyano-N''-[3-[3-(piperidinomethyl)phenoxy]propyl]guanidine Preparation is effected analogously to Example 1, using 0.7 g (2.3 mmol) of N-[3-(4-chlorophenyl)-3-(2-pyridyl)propyl]-N-methyl-1,2-ethanediamine and 0.85 g (2.2 mmol) of N-cyano-O-phenyl-N'-[3-[3-(piperidinomethyl)phenoxy]propyl]isourea as starting materials. Working up by chromatography (eluant: ethyl acetate) analogously to Example 1 yields the purified title compound in the form of a viscous oil; MS (+FAB-method): m/z (rel. int.[%])=602 ([M+H]+, 5), 230 (100); IR (KBr): 2165 cm$^{-1}$ (C≡N). For analytical purposes a sample is converted into the O,O'-ditoluoyltartaric acid salt and recrystallised from ether/isopropanol; m.p.: from 85° C. with decomposition.

EXAMPLE 6

N-cyano-N'-[4-[N-[3-(4-fluorophenyl)-3-(2-pyridyl)propyl]-N-methylamino]-butyl]-N''-[3-[3-(piperidinomethyl)phenoxy]propyl]guanidine Preparation is effected analogously to Example 1, using 0.8 g (2.5 mmol) of N-[3-(4-fluorophenyl)-3-(2-pyridyl)propyl]-N-methyl-1,4-butanediamine and 0.99 g (2.5 mmol) of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int.[%])=614 ([M+H]+, 3), 214 (50.2), 154 ([m-NO$_2$-benzylOH], 100); IR (KBr): 2163 cm$^{-1}$ (C≡N). For analytical purposes a sample is converted into the O,O'-ditoluoyltartaric acid salt and recrystallised from ether/isopropanol; m.p.: 105°-110° C. with decomposition.

EXAMPLE 7

N-cyano-N'-[3-[N-[3-(4-fluorophenyl)-3-(2-pyridyl)propyl]-N-methylamino]propyl]-N''-[3-[3-(piperidinomethyl)phenoxy]propyl]guanidine Preparation is effected analogously to Example 1, using 0.8 g (2.7 mmol) of N-[3-(4-fluorophenyl)-3-(2-pyridyl)propyl]-N-methyl-1,3-propanediamine and 1.04 g (2.6 mmol) of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int.[%])=600 ([M+H]+22.4), 214 (100); IR (KBr): 2164 cm$^{-1}$ (C≡N).

EXAMPLE 8

N-cyano-N'-[2-[N-[3-(4-fluorophenyl)-3-(2-pyridyl)propyl]-N-methylamino]ethyl]-N''-[3-[3-(piperidinomethyl)phenoxy]propyl]guanidine Preparation is effected analogously to Example 1, using 0.7 g (2.4 mmol) of N-[3-(4-fluorophenyl)-3-(2-pyridyl)propyl]-N-methyl-1,2-ethanediamine and 0.95 g (2.4 mmol) of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int.[%])=586 ([M+H]+, 1), 214 (100).

EXAMPLE 9

N-cyano-N'-[4-[N-[3-phenyl-3-(2-pyridyl)propyl]-N-methylamino]butyl]-N''-[3-[3-(piperidinomethyl)phenoxy]propyl]guanidine Preparation is effected analogously to Example 1, using 0.7 g (2.3 mmol) of N-methyl-N-[3-phenyl-3-(2-pyridyl)propyl]-1,4-butanediamine and 0.89 g (2.3 mmol) of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int.[%])=596 ([M+H]+ 7), 196 (100).

EXAMPLE 10

N-cyano-N'-[3-[N-[3-phenyl-3-(2-pyridyl)propyl]-N-methylamino]propyl]-N''-[3-[3-(piperidinomethyl)phenoxy]propyl]guanidine Preparation is effected analogously to Example 1, using 0.57 g (2 mmol) of N-methyl-N-[3-phenyl-3-(2-pyridyl)propyl]-1,3-propanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil; IR (KBr): 2164 cm$^{-1}$ (C≡N).

EXAMPLE 11

N-cyano-N'-[2-[N-[3-phenyl-3-(2-pyridyl)propyl]-N-methylamino]ethyl]-N''-[3-[3-(piperidinomethyl)phenoxy]propyl]guanidine Preparation is effected analogously to Example 1, using 0.7 g (2.6 mmol) of N-methyl-N-[3-phenyl-3-(2-pyridyl)propyl]-1,2-ethanediamine and 1 g (2.5 mmol) of N-cyano-O-phenyl-N'-[3-[3-(piperidinomethyl)phenoxy]propyl]isourea as starting materials. Working up by chromatography (eluant: ethyl acetate) analogously to Example 1 yields the purified title compound in the form of a viscous oil; MS (+FAB method): m/z (rel. int.[%])=568 ([M+H]+ 3), 196 (100).

EXAMPLE 12

N-cyano-N'-[2-[[(2-guanidino-4-thiazolyl)methyl]thio]ethyl]-N''-[2-[N-[3-phenyl-3-(2-pyridyl)propyl]-N-methylamino]ethyl]guanidine Preparation is effected analogously to Example 1, using 0.8 g (3 mmol) of N-methyl-N-[3-phenyl-3-(2-pyridyl)propyl]-1,2-ethanediamine and 1.01 g (2.7 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a viscous oil; MS (+FAB method): m/z (rel. int.[%])=551 ([M+H]+, 2), 196 (100); IR (KBr): 2164 cm$^{-1}$ (C≡N). For analytical purposes a sample is converted into the maleic acid salt and recrystallised from ether/ethanol; m.p.: 115°–116° C. with decomposition.

EXAMPLE 13

N-cyano-N'-[2-[[(2-guanidino-4-thiazolyl)methyl]thio]ethyl]-N''-[3-[N-3-phenyl-3-(2-pyridyl)propyl]-N-methylamino]propyl]guanidine Preparation is effected analogously to Example 1, using 0.85 g (3 mmol) of N-methyl-N-[3-phenyl-3-(2-pyridyl)propyl]-1,3-propanediamine and 1.12 g (3 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a dry foam; MS (+FAB method): m/z (rel. int.[%])=565 ([M+H]+, 2), 196 (100); IR (KBr): 2162 cm$^{-1}$ (C≡N). For analytical purposes a sample is converted into the maleic acid salt and recrystallised from ether/isopropanol; m.p.: 110°–112° C. with decomposition.

EXAMPLE 14

N-cyano-N'-[4-[N-[3-(4-fluorophenyl)-3-(2-pyridyl)propyl]-N-methylamino]butyl]-N''-[2[[(2-guanidino-4-thiazolyl)methyl]thio]ethyl]guanidine Preparation is effected analogously to Example 1, using 0.8 g (2.5 mmol) of N-[3-(4-fluorophenyl)-3-(2-pyridyl)propyl]-N-methyl-1,4-butanediamine and 0.95 g (2.5 mmol) of N-cyano-N'-[2-[[(2-guanidino-4-thiazolyl)methyl]thio]ethyl]-O-phenyl-isourea as starting materials. Working up by chromatography (eluant: methylene chloride/methanol 95+5) analogously to Example 1 yields the purified title compound in the form of a viscous oil; MS (+FAB method): m/z (rel. int.[%])=597 ([M+H]+ 1), 214 (100); IR (KBr): 2162 cm$^{-1}$ (C≡N).

EXAMPLE 15

N-[2-[N-[3-(4-chlorophenyl)-3-(2-pyridyl)propyl]-N-methylamino]ethyl]-N'-cyano-N''-[2-[[(2-guanidino-4-thiazolyl)methyl]thio]ethyl]guanidine Preparation is effected analogously to Example 1, using 0.8 g (2.6 mmol) of N-[3-(4-chlorophenyl)-3-(2-pyridyl)propyl]-N-methyl-1,2-ethanediamine and 0.98 g (2.6 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a dry foam; MS (+FAB method): m/z (rel. int.[%])=585 ([M+H]+, 6), 230 (100); IR (KBr): 2164 cm$^{-1}$ (C≡N). For analytical purposes a sample is converted into the O,O'-ditoluoyltartaric acid salt and recrystallised from ether/isopropanol; m.p.: from 160° C. with decomposition.

EXAMPLE 16

N-[3-[N-[3-(4-chlorophenyl)-3-(2-pyridyl)propyl]-N-methylamino]propyl]-N'-cyano-N''-[2-[[(2-guanidino-4-thiazolyl)methyl]thio]ethyl]guanidine Preparation is effected analogously to Example 1, using 0.8 g (2.5 mmol) of N-[3-(4-chlorophenyl)-3-(2-pyridyl)propyl]-N-methyl-1,3-propanediamine and 0.94 g (2.5 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a dry foam; MS (+FAB method): m/z (rel. int.[%])=599 ([M+H]+,7), 230 (100); IR (KBr): 2161 cm$^{-1}$ (C≡N). For analytical purposes a sample is converted into the O,O'-ditoluoyltartaric acid salt and recrystallised from ether/isopropanol; m.p.: from 160° C. with decomposition.

EXAMPLE 17

N-[4-[N-[3-(4-chlorophenyl)-3-(2-pyridyl)propyl]-N-methylamino]butyl]-N'-cyano-N''-[2-[[(2-guanidino-4-thiazolyl)methyl]thio]ethyl]guanidine Preparation is effected analogously to Example 1, using 0.7 g (2.1 mmol) of N-[3-(4-chlorophenyl)-3-(2-pyridyl)propyl[-N-methyl-1,4-butanediamine and 0.79 g (2.1 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a dry foam; MS (+FAB method): m/z (rel. int.[%])=613 ([M+H]+, 2), 230 (100).

EXAMPLE 18

N-[5-[N-[3-(4-chlorophenyl)-3-(2-pyridyl)propyl]-N-methylamino]pentyl]-N'-cyano-N''-[2-[[(2-guanidino-4-thiazolyl)methyl]thio]ethyl]guanidine Preparation is effected analogously to Example 1, using 0.75 g (2.1 mmol) of N-[3-(4-chlorophenyl)-3-(2-pyridyl)propyl]-N-methyl-1,5-pentanediamine and 0.81 g (2.1 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a dry foam; MS (+FAB method): m/z (rel. int.[%])=627 ([M+H]+, 3), 230 (100); IR (KBr): 2162 cm$^{-1}$ (C≡N). For analytical purposes a sample is converted into the maleic acid salt and recrystallised from ether/ethanol; m.p.: 87°–90° C.

EXAMPLE 19

N-[6-[N-[3-(4-chlorophenyl)-3-(2-pyridyl)propyl]-N-methylamino]hexyl]-N'-cyano-N''-[2-[[(2-guanidino-4-thiazolyl)methyl]thio]ethyl]guanidine Preparation is effected analogously to Example 1, using 0.5 g (1.4 mmol) of N-[3-(4-chlorophenyl)-3-(2-pyridyl)propyl]-N-methyl-1,6-hexanediamine and 0.52 g (1.4 mmol) of N-cyano-N'-[2-[[(2-guanidino-4-thiazolyl)methyl]thio]ethyl]-O-phenyl-isourea as starting materials. Working up by chromatography (eluant: methylene chloride/methanol 95+5) analogously to Example 1 yields the purified title compound in the form of a dry foam; MS (+FAB method): m/z (rel. int.[%])=641 ([M+H]+, 5), 230 (47), 154 (100); IR (KBr): 2161 cm$^{-1}$ (C≡N).

EXAMPLE 20

N-[7-[N-[3-(4-chlorophenyl)-3-(2-pyridyl)propyl]-N-methylamino]heptyl]-N'-cyano-N''-[2-[[(2-guanidino-4-thiazolyl)methyl]thio]ethyl]guanidine Preparation is effected analogously to Example 1, using 0.7 g (1.9 mmol) of N-[3-(4-chlorophenyl)-3-(2-pyridyl)propyl]-N-methyl-1,7-heptanediamine and 0.7 g (1.9 mmol) of N-cyano-N'-[2-[[(2-guanidino-4-thiazolyl)methyl]thio]ethyl]-O-phenyl-isourea as starting materials. Working up by chromatography (eluant: methylene chloride/methanol 95+5) analogously to Example 1 yields the purified title compound in the form of a dry foam; MS (+FAB method): m/z (rel. int.[%])=655 ([M+H]+ 2), 230 (18), 154 (100); IR (KBr): 2161 cm$^{-1}$ (C≡N). For analytical purposes a sample is converted into the O,O'-ditoluoyltartaric acid salt and recrystallised from ether/isopropanol; m.p.: from 150° C. with decomposition.

EXAMPLE 21

N-cyano-N'-[2-[[(2-guanidino-4-thiazolyl)methyl]thio]ethyl]-N''-[4-[N-[2-[[(4-methylphenyl)phenyl-methyl]thio]ethyl]N-methylamino]butyl]guanidine Preparation is effected analogously to Example 1, using 0.87 g (2.5 mmol) of N-methyl-N-[2-[[(4-methylphenyl)phenyl-methyl]thio]ethyl]-1,4-butanediamine and 0.95 g (2.5 mmol) of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a viscous oil; MS (+FAB method): m/z (rel. int.[%])=624 ([M+H]+,6), 181 (100); IR (KBr): 2161 cm$^{-1}$ (C≡N). For analytical purposes a sample is converted into the O,O'-ditoluoyltartaric acid salt and recrystallised from ether/isopropanol; m.p.: 134°-140° C. with decomposition.

EXAMPLE 22

N-[3-[N-[3-(4-fluorophenyl)-3-(2-pyridyl)propyl]-N-methylamino]propyl]-N'-[3-[3-(piperidinomethyl)phenoxy]propyl]-2-nitro-1,1-ethenediamine A mixture of 0.74 g (2.5 mmol) of N-[3-(4-fluorophenyl)-3-(2-pyridyl)propyl]-N-methyl-1,3-propanediamine and an equimolar amount of 1-methylthio-1-[3-[3-(piperidinomethyl)phenoxy]propyl]amino-2-nitroethene is heated under reflux for 12 hours in 20 ml of acetonitrile. The batch is then freed from solvent and the title compound is isolated in the form of a viscous oil by means of preparative thick-layer chromatography (eluant: ethyl acetate/methanol 9+1, ammoniacal atmosphere); MS (+FAB method): m/z (rel. int.[%])=619 ([M+H]+ 2), 214 (100). For analytical purposes a sample is converted into the O,O'-ditoluoyltartaric acid salt and recrystallised from ether/isopropanol; m.p.: from 102° C. with decomposition.

EXAMPLE 23

N-[7-[N-[3-(4-chlorophenyl)-3-(2-pyridyl)propyl]-N-methylamino]heptyl]-N'-[2-[[(2-guanidino-4-thiazolyl)-methyl]thio]ethyl]-2-nitro-1,1-ethenediamine Preparation is effected analogously to Example 22, using 0.83 g (1.7 mmol) of 1-[7-[N-[3-(4-chlorophenyl)-3-(2-pyridyl)propyl]-N-methylamino]heptyl]amino-1-methyl-thio-2-nitro-ethene and 0.5 g (2.1 mmol) of 2-[[(2-guanidino-4-thiazolyl)methyl]thio]ethaneamine as starting materials. Working up by chromatography analogously to Example 1 yields the purified title compound in the form of a dry foam; MS (+FAB method): m/z (rel. int.[%])=674 ([M+H]+ 0.6), 230 (100).

EXAMPLE 24

N-[2-[N-[3-(4-chlorophenyl)-3-(2-pyridyl)propyl]-N-methylamino]ethyl]-N'-[4-[3-(piperidinomethyl)phenoxy]butyl]urea Preparation is effected analogously to Example 63, using 0.8 g (2.6 mmol) of N-[3-(4-chlorophenyl)-3-(2-pyridyl)propyl]-N-methyl-1,2-ethanediamine, an equimolar amount of 1,1'-carbonyldiimidazole and 0.69 g (2.7 mmol) of 4-[3-(piperidinomethyl)phenoxy]butaneamine as starting materials. Working up by chromatography (eluant: methylene chloride) analogously to Example 63 yields the purified title compound in the form of an oil; MS (+FAB method): m/z (rel. int.[%])=592 ([M+H]+, 2), 230 (100); IR (KBr): 1632 cm$^{-1}$ (C=O). For analytical purposes a sample is converted into the O,O'-ditoluoyltartaric acid salt and recrystallised from ether/isopropanol; m.p.: from 124° C. with decomposition.

EXAMPLE 25

N-[5-[N-[3-(4-chlorophenyl)-3-(2-pyridyl)propyl]-N-methylamino]pentyl]-N'-[3-[3-(piperidinomethyl)phenoxy]propyl]urea Preparation is effected analogously to Example 63, using 1.29 g (3.6 mmol) of N-[3-(4-chlorophenyl)-3-(2-pyridyl)propyl]-N-methyl-1,5-pentanediamine, an equimolar amount of 1,1'-carbonyldiimidazole and 1.04 g (4.2 mmol) of 3-[3-(piperidinomethyl)phenoxy]propaneamine as starting materials. Working up by chromatography (eluant: methylene chloride) analogously to Example 63 yields the purified title compound in the form of an oil; MS (+EI-80 eV): m/z (rel. int.[%])=619 ([M])+.,<1), 230 (17) 203 (100); IR (KBr): 1634 cm$^{-1}$ (C=O).

EXAMPLE 26

N-[4-[N-[3-(4-chlorophenyl)-3-(2-pyridyl)propyl]-N-methylamino]butyl]-N'-[3-[3-(piperidinomethyl)phenoxy]propyl]urea Preparation is effected analogously to Example 63, using 0.7 g (2.1 mmol) of N-[3-(4-chlorophenyl)-3-(2-pyridyl)propyl]-N-methyl-1,4-butanediamine, an equimolar amount of 1,1'-carbonyldiimidazole and 0.7 g (2.8 mmol) of 3-[3-(piperidinomethyl)phenoxy]propaneamine as starting materials. Working up by chromatography (eluant: methylene chloride/methanol 95+5) analogously to Example 63 yields the purified title compound in the form of an oil; MS (+FAB method): m/z (rel. int.[%])=606 ([M+H]+, 4), 230 (100); IR (KBr): 1643 cm$^{-1}$ (C=O).

EXAMPLE 27

N-[3-[N-[3-(4-chlorophenyl)-3-(2-pyridyl)propyl]-N-methylamino]porpyl]-N'-[3-[3-(piperidinomethyl)phenoxy]propyl]urea Preparation is effected analogously to Example 63, using 0.7 g (2.2 mmol) of N-[3-(4-chlorophenyl)-3-(2-pyridyl)propyl]-N-methyl-1,3-propanediamine, an equimolar amount of 1,1'-carbonyldiimidazole and 0.55 g (2.2 mmol) of 3-[3-(piperidinomethyl)phenoxy]propaneamine as starting materials. Working up by chromatography analogously to Example 63 yields the purified title compound in the form of an oil. For analytical purposes a sample is converted into the maleic

EXAMPLE 28

N-[2-[N-[3-(4-chlorophenyl)-3-(2-pyridyl)propyl]-N-methylamino]ethyl]-N'-[3-[3-(piperidinomethyl)-phenoxy]propyl]urea Preparation is effected analogously to Example 63, using 0.92 g (3 mmol) of N-[3-(4-chlorophenyl)-3-(2-pyridyl)propyl]-N-methyl-1,2-ethanediamine, an equimolar amount of 1,1'-carbonyldiimidazole and 0.88 g (3.5 mmol) of 3-[3-(piperidinomethyl)phenoxy]propaneamine as starting materials. Working up by chromatography (eluant: ethyl acetate) analogously to Example 63 yields the purified title compound in the form of an oil; MS (+FAB method): m/z (rel. int.[%])=578 ([M+H]+, 2), 230 (38), 78 (100); IR (KBr): 1637 cm$^{-1}$ (C=O). For analytical purposes a sample is converted into the O,O'-ditoluoyltartaric acid salt and recrystallised from ether/isopropanol; m.p.: 99°–105° C.

EXAMPLE 29

N-[4-[N-[3-(4-fluorophenyl)-3-(2-pyridyl)propyl]-N-methylamino]butyl]-N'-[3-[3-(piperidinomethyl)-phenoxy]propyl]urea Preparation is effected analogously to Example 63, using 0.7 g (2.2 mmol) of N-[3-(4-fluorophenyl)-3-(2-pyridyl)propyl]-N-methyl-1,4-butanediamine, an equimolar amount of 1,1'-carbonyldiimidazole and 0.6 g (2.4 mmol) of 3-[3-(piperidinomethyl)phenoxy]propaneamine as starting materials. Working up by chromatography (eluant: ethyl acetate/methanol 95+5) analogously to Example 63 yields the purified title compound in the form of an oil; MS (+FAB method): m/z (rel. int.[%])=590 ([M+H]+17), 214 (100); IR (KBr): 1631 cm$^{-1}$ (C=O).

EXAMPLE 30

N-[3-[N-[3-(4-fluorophenyl)-3-(2-pyridyl)propyl]-N-methylamino]propyl]-N'-[3-[3-(piperidinomethyl)-phenoxy]propyl]urea Preparation is effected analogously to Example 63, using 0.78 g (2.6 mmol) of N-[3-(4-fluorophenyl)-3-(2-pyridyl)propyl]-N-methyl-1,3-propanediamine, an equimolar amount of 1,1'-carbonyldiimidazole and 0.65 g (2.6 mmol) of 3-[3-(piperidinomethyl)phenoxy]propaneamine as starting materials. Working up by chromatography (eluant: ethyl acetate/methanol 9+1) analogously to Example 63 yields the purified title compound in the form of an oil; MS (+FAB method): m/z (rel. int.[%])=576 ([M+H]+,7), 214 (100); IR (KBr): 1649 cm$^{-1}$ (C=O). For analytical purposes a sample is converted into the maleic acid salt and recrystallised from ether/ethanol; m.p.: 65°–67° C.

EXAMPLE 31

N-[2-[N-[3-(4-fluorophenyl)-3-(2-pyridyl)propyl]-N-methylamino]ethyl]-N'-[3-[3-(piperidinomethyl)-phenoxy]propyl]urea Preparation is effected analogously to Example 63, using 1 g (3.5 mmol) of N-[3-(4-fluorophenyl)-3-(2-pyridyl)propyl]-N-methyl-1,2-ethanediamine, an equimolar amount of 1,1'-carbonyldiimidazole and 0.9 g (3.6 mmol) of 3-[3-(piperidinomethyl)phenoxy]propaneamine as starting materials. Working up by chromatography (eluant: methylene chloride) analogously to Example 63 yields the purified title compound in the form of an oil; MS (EI-80 eV): m/z (rel. int.[%])=561 ([M]+., 3), 84 (70), 214 (100). For analytical purposes a sample is converted into the hydrochloride and recrystallised from ether/ethanol; m.p.: 111°–115° C.

EXAMPLE 32

N-[4-[N-[3-phenyl-3-(2-pyridyl)propyl]-N-methylamino]butyl]-N'-[3-[3-(piperidinomethyl)-phenoxy]propyl]urea Preparation is effected analogously to Example 63, using 0.7 g (2.3 mmol) of N-methyl-N-[3-phenyl-3-(2-pyridyl)propyl]-1,4-butanediamine, an equimolar amount of 1,1'-carbonyldiimidazole and 0.7 g (2.8 mmol) of 3-[3-(piperidinomethyl)phenoxy]propaneamine. Working up by chromatography analogously to Example 63 yields the purified title compound in the form of an oil; MS (EI-80 eV): m/z (rel. int.[%])=571 ([M]+, 4), 84 (22), 169 (100).

EXAMPLE 33

N-[3-[N-[3-phenyl-3-(2-pyridyl)propyl]-N-methylamino]propyl]-N'-[3-[3-(piperidinomethyl)-phenoxy]propyl]urea Preparation is effected analogously to Example 63, using 0.74 g (2.6 mmol) of N-methyl-N-[3-phenyl-3-(2-pyridyl)propyl]-1,3-propanediamine, an equimolar amount of 1,1'-carbonyldiimidazole and 0.65 g (2.6 mmol) of 3-[3-(piperidinomethyl)phenoxy]propaneamine as starting materials. Working up by chromatography (eluant: ethyl acetate/methanol 9+1) analogously to Example 63 yields the purified title compound in the form of an oil; MS (+FAB method): m/z (rel. int.[%])=558 ([M+H]+, 11), 196 (100); IR (KBr): 1639 cm$^{-1}$ (C=O). For analytical purposes a sample is converted into the maleic acid salt and recrystallised from ether/ethanol; m.p.: from 70° C. with decomposition.

EXAMPLE 34

N-[2-[N-[3-phenyl-3-(2-pyridyl)propyl]-N-methylamino]ethyl]-N'-[3-[3-(piperidinomethyl)-phenoxy]propyl]urea Preparation is effected analogously to Example 63, using 0.33 g (1.2 mmol) of N-methyl-N-[3-phenyl-3-(2-pyridyl)propyl]-1,2-ethanediamine, an equimolar amount of 1,1'-carbonyldiimidazole and 0.4 g (1.6 mmol) of 3-[3-(piperidinomethyl)phenoxy]propaneamine in 10 ml of absolute tetrahydrofuran as starting materials. Working up by chromatography (eluant: ethyl acetate) analogously to Example 63 yields the purified title compound in the form of an oil; MS (EI-80 eV): m/z (rel. int.[%])=543 ([M]+, 1), 84 (100). For analytical purposes a sample is converted into the hydrochloride and recrystallised from ether/ethanol; m.p.: from 130° C. with decomposition.

EXAMPLE 35

N-[8-[N-[3-(4-chlorophenyl)-3-(2-pyridyl)propyl]-N-methylamino]octyl]-N'-[2-[[(2-guanidino-4-thiazolyl)-methyl]thio]ethyl]urea Preparation is effected analogously to Example 63, using 0.6 g (1.6 mmol) of N-[3-(4-chlorophenyl)-3-(2-pyridyl)propyl]-N-methyl-1,8-octanediamine, an equimolar amount of 1,1'-carbonyldiimidazole and 0.4 g (1.7 mmol) of 2-[[(2-guanidino-4-thiazolyl)methyl]thio]e- thaneamine as starting materials. Working up by chromatography (eluant: chloroform/methanol 9+1) analogously to Example 63 yields the purified title compound in the form of a dry foam; MS (+FAB method, DMSO/MNBA): m/z (rel. int.[%])=645 ([M+H]+,<1), 234 (100); IR (KBr): 1638 cm$^{-1}$ (C=O). For analytical purposes a sample is converted into the O,O'-ditoluoyltartaric acid salt and recrystallised from ether/isopropanol; m.p.: 135°-140° C.

EXAMPLE 36

N-[7-[N-[3-(4-chlorophenyl)-3-(2-pyridyl)propyl]-N-methylamino]heptyl]-N'-[2-[[(2-guanidino-4-thiazolyl)methyl]thio]ethyl]urea Preparation is effected analogously to Example 63, using 0.73 g (1.9 mmol) of N-[3-(4-chlorophenyl)-3-(2-pyridyl)propyl]-N-methyl-1,7-heptanediamine, an equimolar amount of 1,1'-carbonyldiimidazole and 0.45 g (2 mmol) of 2-[[(2-guanidino-4-thiazolyl)methyl]thio]ethaneamine [DE-A-2 817 078, ICI; C.A. 90. 87452d (1979)] as starting materials. Working up by chromatography (eluant: methylene chloride/methanol 9+1) analogously to Example 63 yields the purified title compound in the form of a dry foam; MS (+FAB method): m/z (rel.int.[%])=631 ([M+H]+, 3), 230 (31), 154 (100); IR (KBr): 1605 cm$^{-1}$ (C=O). For analytical purposes a sample is converted into the O,O'-ditoluoyltartaric acid salt and recrystallised from ether/isopropanol; m.p.: 132°-134° C. with decomposition.

The starting material is prepared as follows:

As described in Example 1, a solution of 3-(4-chlorophenyl)-3-(2-pyridyl)propaneamine is reacted to form 3-(4-chlorophenyl)-3-(2-pyridyl)-N-methyl-1-propaneamine [A. Buschauer, J. Med. Chem. 32, 1963 (1989)] which, after purification by column chromatography (ethyl acetate/ammoniacal methanol 99+1), in a batch size of 10-30 mmol is stirred for 2 hours at 60° C. together with an equivalent amount of 7-bromoheptanonitrile and twice the molar excess of Na$_2$CO$_3$ in 20 ml of acetonitrile. When the reaction is complete (TLC monitoring), 20 ml of water are added to the batch, which is extracted several times with toluene. The combined organic extracts are washed with water, dried over Na$_2$SO$_4$ and decolorised for column chromatography using a small amount of silica gel. Concentration by evaporation in vacuo yields the reaction product, 7-[N-[3-(4-chlorophenyl)-3-(2-pyridyl)propyl]-N-methylamino]-heptanonitrile of adequate purity. The nitrile thus produced is dissolved in ether, added dropwise to an ice-cooled stirred suspension of LiAlH$_4$ (1.5 equivalents) in absolute ether (total volume approx. 50 ml) and left for 2 hours at room temperature. When reaction of the educt is complete, water-saturated ether and 2-3 ml of 10% NaOH are added to the batch, which is stirred at room temperature overnight. After removal of the inorganic phases by suction-filtration, the filtrate is concentrated by evaporation in vacuo and the resulting N-[3-(4-chlorophenyl)-3-(2-pyridyl)propyl]-N-methyl-1,7-heptanediamine, if sufficiently pure, is reacted further or is isolated by means of preparative thick-layer chromatography.

EXAMPLE 37

N-[6-[N-[3-(4-chlorophenyl)-3-(2-pyridyl)propyl]-N-methylamino]hexyl]-N'-[2-[[(2-guanidino-4-thiazolyl)methyl]thio]ethyl]urea Preparation is effected analogously to Example 63, using 0.9 g (2.5 mmol) of N-[3-(4-chlorophenyl)-3-(2-pyridyl)propyl]-N-methyl-1,6-hexanediamine, an equimolar amount of 1,1'-carbonyldiimidazole and 0.6 g (2.6 mmol) of 2-[[(2-guanidino-4-thiazolyl)methyl]thio]ethaneamine as starting materials. Working up by chromatography (eluant: methylene chloride) analogously to Example 63 yields the purified title compound in the form of an oil; MS (+FAB method): m/z (rel. int.[%])=617 ([M+H]+, 6), 230 (100), 155 (28); IR (KBr): 1641 cm$^{-1}$ (C=O).

EXAMPLE 38

N-[5-[N-[3-(4-chlorophenyl)-3-(2-pyridyl)propyl]-N-methylamino]pentyl]-N'-[2-[[(2-guanidino-4-thiazolyl)methyl]thio]ethyl]urea Preparation is effected analogously to Example 63, using 1.04 g (3 mmol) of N-[3-(4-chlorophenyl)-3-(2-pyridyl)propyl]-N-methyl-1,5-pentanediamine, an equimolar amount of 1,1'-carbonyldiimidazole and 0.75 g (3.3 mmol) of 2-[[(2-guanidino-4-thiazolyl)methyl]thio]ethaneamine as starting materials. Working up by chromatography (eluant: chloroform/methanol 9+1) analogously to Example 63 yields the purified title compound in the form of a dry foam; MS (+FAB method): m/z (rel. int.[%])=603 ([M+H]+, 1), 155 (18), 230 (100); IR (KBr): 1640 cm$^{-1}$ (C=O).

EXAMPLE

N-[4-[N-[3-(4-chlorophenyl)-3-(2-pyridyl)propyl]-N-methylamino]butyl]-N'-[2-[[(2-guanidino-4-thiazolyl)methyl]thio]ethyl]urea Preparation is effected analogously to Example 63, using 0.75 g (2 mmol) of N-[3-(4-chlorophenyl)-3-(2-pyridyl)propyl]-N-methyl-1,4-butanediamine, an equimolar amount of 1,1'-carbonyldiimidazole and 0.54 g (2.3 mmol) of 2-[[(2-guanidino-4-thiazolyl)methyl]thio]ethaneamine as starting materials. Working up by chromatography (eluant: methylene chloride/methanol 9+1) analogously to Example 63 yields the purified title compound in the form of a dry foam; MS (+FAB method): m/z (rel. int.[%])=589 ([M+H]+, 2), 230 (100); IR (KBr): 1650 cm$^{-1}$ (C=O). For analytical purposes a sample is converted into the maleic acid salt and recrystallised from ether/ethanol; m.p.: from 90° C. with decomposition.

EXAMPLE 40

N-[3-[N-[3-(4-chlorophenyl)-3-(2-pyridyl)propyl]-N-methylamino]propyl]-N'-[2-[[(2-guanidino-4-thiazolyl)methyl]thio]ethyl]urea Preparation is effected analogously to Example 63, using 0.9 g (2.8 mmol) of N-[3-(4-chlorophenyl)-3-(2-pyridyl)propyl]-N-methyl-1,3-propanediamine, an equimolar amount of 1,1'-carbonyldiimidazole and 0.73 g (3.1 mmol) of 2-[[(2-guanidino-4-thiazolyl)methyl]thio]ethaneamine as starting materials. Working up by chromatography (eluant: ethyl acetate/methanol 85+15) analogously to Example 63 yields the purified title compound in the form of a dry foam; MS (+FAB method): m/z (rel. int.[%])=575 ([M+H]+, 3), 155 (22), 230 (100); IR (KBr): 1646 cm$^{-1}$ (C=O).

EXAMPLE 41

N-[2-[N-[3-(4-chlorophenyl)-3-(2-pyridyl)propyl]-N-methylamino]ethyl]-N'-[2-[[(2-guanidino-4-thiazolyl)-methyl]thio]ethyl]urea Preparation is effected analogously to Example 63, using 0.9 g (2.9 mmol) of N-[3-(4-chlorophenyl)-3-(2-pyridyl)propyl]-N-methyl-1,2-ethanediamine, an equimolar amount of 1,1'-carbonyldiimidazole and 0.75 g (3.2 mmol) of 2-[[(2-guanidino-4-thiazolyl)methyl]thio]ethaneamine as starting materials. Working up by chromatography (eluant: methylene chloride/methanol 95+5) analogously to Example 63 yields the purified title compound in the form of an oil; MS (+FAB method): m/z (rel. int.[%])=561 ([M+H]+, 3), 155 (26), 230 (100); IR (KBr): 1650 cm+1 (C=O). For analytical purposes a sample is converted into the O,O'-ditoluoyltartaric acid salt and recrystallised from ether-/isopropanol; m.p.: from 140° C. with decomposition.

EXAMPLE 42

N-[7-[N-[3-(4-fluorophenyl)-3-(2-pyridyl)propyl]-N-methylamino]heptyl]-N'-[2-[[(2-guanidino-4-thiazolyl)-methyl]thio]ethyl]urea Preparation is effected analogously to Example 63, using 0.9 g (2.5 mmol) of N-[3-(4-fluorophenyl)-3-(2-pyridyl)propyl]-N-methyl-1,7-heptanediamine, an equimolar amount of 1,1'-carbonyldiimidazole and 0.65 g (2.8 mmol) of 2-[[(2-guanidino-4-thiazolyl)methyl]thio]ethaneamine as starting materials. Working up by chromatography (eluant: methylene chloride) analogously to Example 63 yields the purified title compound in the form of a dry foam; MS (+FAB method): m/z (rel. int.[%])=615 ([M+H]+ 2), 214 (100); IR (KBr): 1632 cm−1 (C=O).

EXAMPLE 43

N-[4-[N-[3-(4-fluorophenyl)-3-(2-pyridyl)propyl]-N-methylamino]butyl]-N'-[2-[[(2-guanidino-4-thiazolyl)-methyl]thio]ethyl]urea Preparation is effected analogously to Example 63, using 0.95 g (3.5 mmol) of N-[3-(4-fluorophenyl)-3-(2-pyridyl)propyl]-N-methyl-1,4-butanediamine, an equimolar amount of 1,1'-carbonyldiimidazole and 0.82 g (3.5 mmol) of 2-[[(2-guanidino-4-thiazolyl)methyl]thio]ethaneamine as starting materials. Working up by chromatography (eluant: ethyl acetate/methanol 9+1) analogously to Example 63 yields the purified title compound in the form of a dry foam; MS (+FAB method): m/z (rel. int.[%])=573 ([M+H]+ 2), 214 (100); IR (KBr): 1632 cm−1 (C=O). For analytical purposes a sample is converted into the O,O'-ditoluoyltartaric acid salt and recrystallised from ether/isopropanol; m.p.: from 120° C. with decomposition.

EXAMPLE 44

N-[2-[[(2-guanidino-4-thiazolyl)methyl]thio]ethyl]-N'-[7-[N-[3-phenyl-3-(2-pyridyl)propyl]-N-methylamino]heptyl]urea Preparation is effected analogously to Example 63, using 0.85 g (2.5 mmol) of N-methyl-N-[3-phenyl-3-(2-pyridyl)propyl]-1,7-heptanediamine, an equimolar amount of 1,1'-carbonyldiimidazole and 0.65 g (2.8 mmol) of 2-[[(2-guanidino-4-thiazolyl)methyl]thio]ethaneamine as starting materials. Working up by chromatography (eluant: methylene chloride) analogously to Example 63 yields the purified title compound in the form of an oil; MS (+FAB method): m/z (rel. int.[%])=597 ([M+H]+, 7), 196 (100); IR (KBr): 1655 cm−1 (C=O).

EXAMPLE 45

N-[2-[[(2-guanidino-4-thiazolyl)methyl]thio]ethyl]-N'-[4-[N-[3-phenyl-3-(2-pyridyl)propyl]-N-methylamino]butyl]urea Preparation is effected analogously to Example 63, using 0.89 g (3 mmol) of N-methyl-N-[3-phenyl-3-(2-pyridyl)propyl]-1,4-butanediamine, an equimolar amount of 1,1'-carbonyldiimidazole and 0.75 g (3.2 mmol) of 2-[[(2-guanidino-4-thiazolyl)methyl]thio]ethaneamine as starting materials. Working up by chromatography (eluant: chloroform/methanol 9+1) analogously to Example 63 yields the purified title compound in the form of a dry foam; MS (+FAB method): m/z (rel. int.[%])=555 ([M+H]+ 1), 196 (100); IR (KBr): 1610 cm−1 (C=O). For analytical purposes a sample is converted into the maleic acid salt and recrystallised from ether/ethanol; m.p.: from 80° C. with decomposition.

EXAMPLE 46

N-[2-[[(2-guanidino-4-thiazolyl)methyl]thio]ethyl]-N'-[3-[N-[3-phenyl-3-(2-pyridyl)propyl]-N-methylamino]propyl]urea Preparation is effected analogously to Example 63, using 0.85 g (3 mmol) of N-methyl-N-[3-phenyl-3-(2-pyridyl)propyl]-1,3-propanediamine, an equimolar amount of 1,1'-carbonyldiimidazole and 0.75 g (3.2 mmol) of 2-[[(2-guanidino-4-thiazolyl)methyl]thio]ethaneamine as starting materials. Working up by chromatography (eluant: chloroform/methanol 9+1) analogously to Example 63 yields the purified title compound in the form of an oil; MS (+FAB method): m/z (rel. int. [%])=541 ([M+H]+, 2), 196 (100); IR (KBr): 1650 cm−1 (C=O). For analytical purposes a sample is converted into the maleic acid salt and recrystallised from ether/ethanol; m.p.: 95°-98° C.

EXAMPLE 47

N-[2-[[(2-guanidino-4-thiazolyl)methyl]thio]ethyl]-N'-[2-[N-[3-phenyl-3-(2-pyridyl)propyl]-N-methylamino]ethyl]urea Preparation is effected analogously to Example 63, using 1 g (3.7 mmol) of N-methyl-N-[3-phenyl-3-(2-pyridyl)propyl]-1,2-ethanediamine, an equimolar amount of 1,1'-carbonyldiimidazole and 1.15 g (5 mmol) of 2-[[(2-guanidino-4-thiazolyl)methyl]thio]ethaneamine as starting materials. Working up by chromatography (eluant: ethyl acetate/methanol 9+1) analogously to Example 63 yields the purified title compound in the form of a dry foam; MS (+FAB method): m/z (rel. int. [%])=527 ([M+H]+ 3), 196 (100).

EXAMPLE 48

N-[7-[N-[3-(4-chlorophenyl)-3-(2-pyridyl)propyl]-N-methylamino]heptyl]-N'-[2-[[(2-guanidino-4-thiazolyl)-methyl]thio]ethyl]thiourea Preparation is effected analogously to Example 99, using 0.84 g (2.2 mmol) of N-3-(4-chlorophenyl)-3-(2-pyridyl)propyl]-N-methyl-1,7-heptanediamine and 0.56 g (2.4 mmol) of 2-[[(2-guanidino-4-thiazolyl)methyl]thio]ethaneamine as starting materials. Working up by chromatography (eluant: chloroform/methanol 9+1) analogously to Example 99 yields the purified title compound in the form of a dry foam; MS (+FAB method): m/z (rel. int. [%])=647 ([M+H]+, 7), 230 (100).

EXAMPLE 49

N-[4-[N-[3-(4-chlorophenyl)-3-(2-pyridyl)propyl]-N-methylamino]butyl]-N'-[2-[[(5-methylimidazol-4-yl)methyl]thio]ethyl]urea Preparation is effected analogously to Example 63, using 0.8 g (2.4 mmol) of N-[3-(4-chlorophenyl)-3-(2-pyridyl)propyl]-N-methyl-1,4-butanediamine, an equimolar amount of 1,1'-carbonyldiimidazole and 0.5 g (2.9 mmol) of 2-[[(5-methylimidazol-4-yl)methyl]thio]ethaneamine [R. W. Brimblecombe et al., J. Int. Med. Res. 3, 86 (1975)] as starting materials. Working up by chromatography (eluant: ethyl acetate/methanol 9+1) analogously to Example 63 yields the purified title compound in the form of a crystalline solid that is recrystallised from ether; m.p.: 97°-98° C.; MS (+FAB method): m/z (rel. int.[%])=529 ([M+H]+, 10), 230 (100); IR (KBr): 1643 cm$^{-1}$ (C=O).

EXAMPLE 50

N-[3-[N-[3-(4-chlorophenyl)-3-(2-pyridyl)propyl]-N-methylamino]propyl]-N'-[2-[[(5-methylimidazol-4-yl)methyl]thio]ethyl]urea Preparation is effected analogously to Example 63, using 0.8 g (2.5 mmol) of N-[3-(4-chlorophenyl)-3-(2-pyridyl)propyl]-N-methyl-1,3-propanediamine, an equimolar amount of 1,1'-carbonyldiimidazole and 0.5 g (2.9 mmol) of 2-[[(5-methylimidazol-4-yl)methyl]thio]ethaneamine as starting materials. Working up by chromatography (eluant: ethyl acetate/methanol 9+1) analogously to Example 63 yields the purified title compound in the form of a crystalline solid; m.p.(ether): 102°-104° C.; MS (+FAB method): m/z (rel. int.[%])=515 ([M+H]+, 10), 95 (75), 230 (100).

EXAMPLE 51

N-[2-[N-[3-(4-chlorophenyl)-3-(2-pyridyl)propyl]-N-methylamino]ethyl]-N'-[2-[[(5-methylimidazol-4-yl)methyl]thio]ethyl]urea Preparation is effected analogously to Example 63, using 0.8 g (2.6 mmol) of N-[3-(4-chlorophenyl)-3-(2-pyridyl)propyl]-N-methyl-1,2-ethanediamine, an equimolar amount of 1,1'-carbonyldiimidazole and 0.5 g (2.8 mmol) of 2-[[(5-methylimidazol-4-yl)methyl]thio]ethaneamine as starting materials. Working up by chromatography (eluant: ethyl acetate/methanol 9+1) analogously to Example 63 yields the purified title compound in the form of a crystalline solid; m.p.(ether): 114° C.; MS (+FAB method): m/z (rel. int.[%])=501 ([M+H]+, 15), 95 (63), 230 (100); IR (KBr): 1640 cm$^{-1}$ (C=O).

EXAMPLE 52

N-cyano-N'-[2-[N-[2-[N-(4-methoxybenzyl)-N-(2-pyridyl)amino]ethyl]-N-methylamino]ethyl]-N''-[3-[3-(piperidinomethyl)phenoxy]propyl]guanidine Preparation is effected analogously to Example 1, using 0.53 g (1.7 mmol) of N-[2-[N-(4-methoxybenzyl)-N-(2-pyridyl)amino]ethyl]-N-methyl-1,2-ethanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil which crystallises from absolute ether at −20° C.; MS (EI 70 eV): m/z (rel. int.[%])=612 ([M]+, 1); IR (KBr): 2164 cm$^{-1}$ (C≡N); m.p.: 88° C. (ether).

The starting material is prepared as follows:

11.23 g (43.64 mmol) of 2-[N-(2-aminoethyl)-N-(4-methoxybenzyl)-amino]pyridine [U.S. Pat. No. 4,532,246 (Dec. 20, 1983); C.A. 102, 6208v (1984)] are dissolved in ether and provided with an underlayer of 10% sodium hydroxide solution. While stirring and cooling with ice-water, 4.73 g (43.64 mmol) of chloroformic acid ethyl ester are added dropwise to the two-phase system in such a manner that the cloudiness so produced first has to dissolve before further ester can be added dropwise. When the reaction is complete the phases are separated, the ethereal phase is dried with Na$_2$SO$_4$ and the ether is distilled off under a weak vacuum to yield N-(4-methoxybenzyl)-N-(2-pyridyl)-2-aminoethaneamino acid ethyl ester in the form of a colourless oil. While cooling with ice and stirring, the oil, dissolved in 20 ml of absolute THF, is introduced slowly into a suspension of 2.28 g (60 mmol) of LiAlH$_4$ in 100 ml of absolute ether. The reaction batch is stirred for 30 min at room temperature and then heated under reflux for a further 1 hour. After cooling, the batch is hydrolysed, while cooling with ice, with water-saturated ether and the dropwise addition of a small amount of 10% sodium hydroxide solution, until the exothermic reaction has ceased and a white precipitate forms. The batch is stirred for a further 30 min and suction-filtered and the precipitate is washed several times with ether.

The filtrate is washed with water, dried over Na$_2$SO$_4$ and concentrated to dryness in vacuo to yield N-(4-methoxybenzyl)-N-(2-pyridyl)-N'-methyl-1,2-ethanediamine which is then heated for 2 hours at 80° C. with the equimolar amount of chloroacetonitrile, three times the molar amount of Na$_2$CO$_3$ and a spatula tip of KI in 60 ml of anhydrous DMF. The reaction batch is cooled to room temperature and then water is added until the precipitate has dissolved. The batch is extracted with toluene. The combined organic phases are dried with MgSO$_4$ and the toluene is distilled off in vacuo. The resulting brownish oil is dissolved in 20 ml of absolute THF and while cooling with ice and stirring is introduced slowly into a suspension of twice the molar amount of LiAlH$_4$ in 50 ml of absolute ether. After stirring for 30 min, the batch is hydrolysed, while cooling with ice, with water-saturated ether and the dropwise addition of a small amount of 10% sodium hydroxide solution until the exothermic reaction has ceased and a white precipitate forms. The batch is stirred for a further 30 min and suction-filtered and the precipitate is washed several times with ether. The filtrate is washed with water, dried over Na$_2$SO$_4$ and concentrated to dryness in vacuo to yield N-[2-]N-(4-methoxybenzyl)-N-(2-pyridyl)amino]ethyl]-N-methyl-1,2-ethanediamine of sufficient purity for the subsequent reaction.

EXAMPLE 53

N-cyano-N'-[3-[N-[2-[N-(4-methoxybenzyl)-N-(2-pyridyl)amino]ethyl]-N-methylamino]propyl]-N''-[3-[3-(piperidinomethyl)phenoxy]propyl]guanidine Preparation is effected analogously to Example 1, using 0.52 g (1.6 mmol) of N-[2-[N-(4-methoxybenzyl)-N-(2-pyridyl)amino]ethyl]-N-methyl-1,3-propanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil which crystallises from absolute ether at −20° C.; MS (+FAB method): m/z (rel. int. [%])=627 ([M+H]+, 6), 241 (11), 121 (100); IR (KBr): 2165 cm$^{-1}$ (C≡N); m.p.: 62°–65° C. (ether).

EXAMPLE 54

N-cyano-N'-[4-[N-[2-[N-(4-methoxybenzyl)-N-(2-pyridyl)amino]ethyl]-N-methylamino]butyl]-N''-[3-[3-(piperidinomethyl)phenoxy]propyl]guanidine Preparation is effected analogously to Example 1, using 0.53 g (1.5 mmol) of N-[2-N-(4-methoxybenzyl)-N-(2-pyridyl)amino]ethyl]-N-methyl-1,4-butanediamine and the equimolar amount of N-cyano-O-phenyl-N'-[3-[3-(piperidinomethyl)phenoxy]propyl]isourea as starting materials. Chromatographic working-up analogously to Example 1 yields the purified title compound in the form of a viscous oil. For analytical purposes a sample is converted into the tartaric acid salt and recrystallised from ether/ethanol/isopropanol; MS (+FAB method): m/z (rel. int. [%])=641 ([M+H]+, 1), 241 (7), 121 (100); IR (KBr): 2166 cm$^{-1}$ (C≡N); m.p.: 106°–108° C. (ether/ethanol/isopropanol).

EXAMPLE 55

N-cyano-N'-[6-[N-[2-[N-(4-methoxybenzyl)-N-(2-pyridyl)amino]ethyl]-N-methylamino]hexyl]-N''-[3-[3-(piperidinomethyl)phenoxy]propyl]guanidine Preparation is effected analogously to Example 1, using 0.56 g (1.52 mmol) of N-[2-[N-(4-methoxybenzyl)-N-(2-pyridyl)amino]ethyl]-N-methyl-1,6-hexanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int. [%])=669 ([M+H]+, 5), 121 (100); IR (KBr): 2163 cm$^{-1}$ (C≡N). For analytical purposes a sample is converted into the tartaric acid salt in an ether/ethanol solvent mixture; m.p.: 79° C. (ether/ethanol).

EXAMPLE 56

N-cyano-N'-[2-[N-[2-[N-(4-fluorobenzyl)-N-(2-pyridyl)amino]ethyl]-N-methylamino]ethyl]-N''-[3-[3-(piperidinomethyl)phenoxy]propyl]guanidine Preparation is effected analogously to Example 1, using 0.30 g (1.0 mmol) of N-[2-[N-(4-fluorobenzyl)-N-(2-pyridyl)amino]ethyl]-N-methyl-1,2-ethanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int. [%])=601 ([M+H]+, 7), 76 (100); IR (KBr): 2169 cm$^{-1}$ (C≡N). For further analysis, a portion of the compound is converted into the tartaric acid salt and recrystallised from ethanol/petroleum ether; m.p.: 106° C. (ethanol/petroleum ether).

EXAMPLE 57

N-cyano-N'-[3-[N-[2-[N-(4-fluorobenzyl)-N-(2-pyridyl)amino]ethyl]-N-methylamino]propyl]-N''-[3-[3-(piperidinomethyl)phenoxy]propyl]guanidine Preparation is effected analogously to Example 1, using 0.63 g (2.0 mmol) of N-[2-[N-(4-fluorobenzyl)-N-(2-pyridyl)amino]ethyl]-N-methyl-1,3-propanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int. [%])=615 ([M+H]+, 14), 229 (100), 109 (96); IR (KBr): 2167 cm$^{-1}$ (C≡N). For further analysis, a portion of the compound is converted into the tartaric acid salt in an ethanol/ether solvent mixture; m.p.: 65°–68° C. (ethanol/ether).

EXAMPLE 58

N-cyano-N'-[4-[N-[2-[N-(4-fluorobenzyl)-N-(2-pyridyl)amino]ethyl]-N-methylamino]butyl]-N''-[3-[3-(piperidinomethyl)phenoxy]propyl]guanidine Preparation is effected analogously to Example 1, using 0.33 g (1.0 mmol) of N-[2-[N-(4-fluorobenzyl)-N-(2-pyridyl)amino]ethyl]-N-methyl-1,4-butanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int. [%])=629 ([M+H]+, 5), 229 (84), 109 (100); IR (KBr): 2166 cm$^{-1}$ (C≡N). For further analysis, a portion of the compound is converted into the tartaric acid salt and recrystallised from ethanol/acetonitrile/isopropanol; m.p. 84°–86° C. (ethanol/acetonitrile/isopropanol).

EXAMPLE 59

N-cyano-N'-[5-[N-[2-[N-(4-fluorobenzyl)-N-(2-pyridyl)amino]ethyl]-N-methylamino]pentyl]-N''-[3-[3-(piperidinomethyl)phenoxy]propyl]guanidine Preparation is effected analogously to Example 1, using 0.54 g (1.6 mmol) of N-[2-[N-(4-fluorobenzyl)-N-(2-pyridyl)amino]ethyl]-N-methyl-1,5-pentanediamine and the equimolar amount of N-cyano-O-phenyl-N'-[3-[3-(piperidinomethyl)phenoxy]propyl]isourea as starting materials. Working up by chromatography analogously to Example 1 yields the purified title compound in the form of a viscous oil; MS (+FAB method): m/z (rel. int. %]) =643 ([M+H]+, 7), 229 (54), 154 ([m-NO$_2$-benzylOH] 100); IR (KBr): 2165 cm$^{-1}$ (C≡N). For further analysis, a portion of the compound is converted into the tartaric acid salt which forms a dry foam under reduced pressure.

EXAMPLE 60

N-cyano-N'-[6-[N-[2-[N-(4-fluorobenzyl)-N-(2-pyridyl)amino]ethyl]-N-methylamino]hexyl]-N''-[3-[3-(piperidinomethyl)phenoxy]propyl]guanidine Preparation is effected analogously to Example 1, using 0.33 g (0.9 mmol) of N-[2-[N-(4-fluorobenzyl)-N-(2-pyridyl)amino]ethyl]-N-methyl-1,6-hexanediamine and the equimolar amount of N-cyano-O-phenyl-N'-[3-(3-(piperidinomethyl)phenoxy]propyl]isourea as starting materials. Chromatographic working-up analogously to Example 1 yields the purified title compound in the form of a viscous oil; MS (+FAB method): m/z (rel. int. [%])=657 ([M+H]+, 11), 229 (100); IR (KBr): 2164 cm$^{-1}$ (C≡N). For further analysis, a portion of the compound is converted into the tartaric acid salt in an ethanol/ether solvent mixture; m.p.: 58° C. (ethanol/ether).

EXAMPLE 61

N-cyano-N'-[7-[N-[2-[N-(4-fluorobenzyl)-N-(2-pyridyl-)amino]ethyl]-N-methylamino]heptyl]-N''-[3-[3-(piperidinomethyl)phenoxy]propyl]guanidine Preparation is effected analogously to Example 1, using 0.48 g (1.3 mmol) of N-[2-[N-(4-fluorobenzyl)-N-(2-pyridyl)amino]ethyl]-N-methyl-1,7-heptanediamine and the equimolar amount of N-cyano-O-phenyl-N'-[3-[3-(piperidinomethyl)phenoxy]propyl]isourea as starting materials. Chromatographic working-up analogously to Example 1 yields the purified title compound in the form of a viscous oil; MS (+FAB method): m/z (rel. int. [%])=671 ([M+H]+, 3), 229 (100); IR (KBr): 2164 cm$^{-1}$ (C≡N). For further analysis, a portion of the compound is converted into the O,O'-ditoluoyltartaric acid salt and recrystallised from isopropanol/ether; m.p.: 96°-98° C. (isopropanol/ether).

EXAMPLE 62

N-cyano-N'-[3-[N-[2-[N-(4-fluorobenzyl)-N-(2-pyridyl-)amino]ethyl]-N-methylamino]propyl]-N''-[4-[3-(piperidinomethyl)phenoxy]butyl]guanidine Preparation is effected analogously to Example 1, using 0.50 g (1.6 mmol) of N-[2-[N-(4-fluorobenzyl)-N-(2-pyridyl)amino]ethyl]-N-methyl-1,3-propanediamine and the equimolar amount of N-cyano-O-phenyl-N'-[4-[3-(piperidinomethyl)phenoxy]butyl]isourea as starting materials. Working up by chromatography analogously to Example 1 yields the purified title compound in the form of a viscous oil; MS (+FAB method): m/z (rel. int. [%])=629 ([M+H]+, 18), 229 (98), 109 (100); IR (KBr): 2164 cm$^{-1}$ (C≡N). For further analysis, a portion of the compound is converted into the O,O'-ditoluoyltartaric acid salt and recrystallised from isopropanol/ether; m.p.: 102°-105° C. (isopropanol/ether).

EXAMPLE 63

N-[2-[N-[2-[N-(4-methoxybenzyl)-N-(2-pyridyl-)amino]ethyl]-N-methylamino]ethyl]-N'-[3-[3-(piperidinomethyl)phenoxy]propyl]urea 0.53 g (1.7 mmol) of N-[2-[N-(4-methoxybenzyl)-N-(2-pyridyl)amino]-ethyl]-N-methyl-1,2-ethanediamine is dissolved in 2.5 ml of absolute THF and, while stirring, is added dropwise in the course of 30 minutes to a solution, cooled to 0° C., of 0.27 g (1.7 mmol) of 1,1'-carbonyldiimidazole in 9 ml of absolute THF in such a manner that the temperature of the reaction batch remains at 0° C. Stirring of the solution at 0° C. is continued until the amine has reacted completely to form the isocyanate (TLC monitoring). An equimolar solution of 3-[3-(piperidinomethyl)phenoxy]propylamine in 5 ml of absolute THF is added dropwise to the isocyanate solution. The reaction batch is stirred at room temperature for 24 hours. Water is then added to the batch, which is stirred for 30 minutes and extracted with methylene chloride. The organic phases are combined and dried with Na$_2$SO$_4$ and the solvent is distilled off under reduced pressure. The residue is purified by rotation chromatography to yield the purified title compound in the form of a viscous oil. MS(+FAB method): m/z (rel. int. [%])=589 ([M+H]+, 1), 241 (10), 121 (100) IR (KBr): 1639 cm$^{-1}$ (C=O).

EXAMPLE 64

N-[3-[N-[2-[N-(4-methoxybenzyl)-N-(2-pyridyl-)amino]ethyl]-N-methylamino]propyl]-N'-[3-[3-(piperidinomethyl)phenoxy]propyl]urea Preparation is effected analogously to Example 63, using 0.54 g (1.65 mmol) of N-[2-[N-(4-methoxybenzyl)-N-(2-pyridyl)amino]ethyl]-N-methyl-1,3-propanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int. [%])=603 ([M+H]+, 10), 121 (100); IR (KBr): 1639 cm$^{-1}$ (C=O). For further analysis, a portion of the compound is converted into the O,O'-ditoluoyltartaric acid salt and recrystallised from isopropanol/ether; m.p.: 120° C. (isopropanol/ether).

EXAMPLE 65

N-[4-[N-[2-[N-(4-methoxybenzyl)-N-(2-pyridyl-)amino]ethyl]-N-methylamino]butyl]-N'-[3-[3-(piperidinomethyl)phenoxy]propyl]urea Preparation is effected analogously to Example 63, using 0.55 g (1.6 mmol) of N-[2-[N-(4-methoxybenzyl)-N-(2-pyridyl)amino]ethyl]-N-methyl-1,4-butanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int. [%])=617 ([M+H]+, 1), 121 (100); IR (KBr): 1603 cm$^{-1}$ (C=O). For further analysis, a portion of the compound is converted into the picric acid salt and recrystallised from ethanol; m.p.: 68°-72° C. (ethanol).

EXAMPLE 66

N-[6-[N-[2-[N-(4-methoxybenzyl)-N-(2-pyridyl-)amino]ethyl]-N-methylamino]hexyl]-N'-[3-[3-(piperidinomethyl)phenoxy]propyl]urea Preparation is effected analogously to Example 63, using 0.58 g (1.5 mmol) of N-[2-[N-(4-methoxybenzyl)-N-(2-pyridyl)amino]ethyl]-N-methyl-1,6-hexanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int. [%])=645 ([M+H]+, 8), 121 (100); IR (KBr): 1635 cm$^{-1}$ (C=O). For further analysis, a portion of the compound is converted into the tartaric acid salt in an ethanol/ether solvent mixture; m.p.: 75° C. (ethanol/ether).

EXAMPLE 67

N-[2-[N-[2-[N-(4-fluorobenzyl)-N-(2-pyridyl)amino]ethyl]-N-methylamino]ethyl]-N'-[3-[3-(piperidinomethyl)phenoxy]propyl]urea Preparation is effected analogously to Example 63, using 0.42 g (1.0 mmol) of N-[2-[N-(4-fluorobenzyl)-N-(2-pyridyl)amino]ethyl]-N-methyl-1,2-ethanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int. [%])=577 ([M+H]+, 12), 229 (99), 109 (100); IR (KBr): 1640 cm$^{-1}$ (C=O). For further analysis, a portion of the compound is converted into the tartaric acid salt and recrystallised from isopropanol/ether/petroleum ether; m.p.: 68° C. (isopropanol/ether/petroleum ether).

EXAMPLE 68

N-[3-[N-[2-[N-(4-fluorobenzyl)-N-(2-pyridyl)amino]ethyl]-N-methylamino]propyl]-N'-[3-[3-(piperidinomethyl)phenoxy]propyl]urea Preparation is effected analogously to Example 63, using 0.63 g (2.0 mmol) of N-[2-[N-(4-fluorobenzyl)-N-(2-pyridyl)amino]ethyl]-N-methyl-1,3-propanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int.[%])=591 ([M+H]+, 7), 229 (86), 109 (100). For further analysis, a portion of the compound is converted into the hydrochloric acid salt and is extracted from ether in the form of a dry foam by stirring; m.p.: 123°-125° C. (ether).

EXAMPLE 69

N-[4-[N-[2-[N-(4-fluorobenzyl)-N-(2-pyridyl)amino]ethyl]-N-methylamino]butyl]-N'-[3-[3-(piperidinomethyl)phenoxy]propyl]urea Preparation is effected analogously to Example 63, using 0.45 g (1.0 mmol) of N-[2-[N-(4-fluorobenzyl)-N-(2-pyridyl)amino]ethyl]-N-methyl-1,4-butanediamine and the equimolar amounts of 1,1'-carbonyldiimidazole and 3-[3-(piperidinomethyl)phenoxy]propylamine as starting materials. Chromatographic working-up analogously to Example 63 yields the purified title compound in the form of a viscous oil; MS (+FAB method): m/z (rel. int. [%])=605 ([M+H]+, 8), 109 (100); IR (KBr): 1641 cm$^{-1}$ (C=O). For further analysis, a portion of the compound is converted into the tartaric acid salt and recrystallised from isopropanol/ether/petroleum ether; m.p.: 69° C. (isopropanol/ether/petroleum ether).

EXAMPLE 70

N-[5-[N-[2-[N-(4-fluorobenzyl)-N-(2-pyridyl)amino]ethyl]-N-methylamino]-pentyl]-N'-[3-[3-(piperidinomethyl)phenoxy]propyl]urea Preparation is effected analogously to Example 63, using 0.51 g (1.5 mmol) of N-[2-[N-(4-fluorobenzyl)-N-(2-pyridyl)amino]ethyl]-N-methyl-1,5-pentanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int. [%])=619 ([M+H]+, 3), 77 (100); IR (KBr): 1634 cm$^{-1}$ (C=O). For further analysis, a portion of the compound is converted into the tartaric acid salt and recrystallised from isopropanol/ether/petroleum ether; m.p.: 63° C. (isopropanol/ether/petroleum ether).

EXAMPLE 71

N-[6-[N-[2-[N-(4-fluorobenzyl)-N-(2-pyridyl)amino]ethyl]-N-methylamino]hexyl]-N'-[3-[3-(piperidinomethyl)phenoxy]propyl]urea Preparation is effected analogously to Example 63, using 0.50 g (1.4 mmol) of N-[2-[N-(4-fluorobenzyl)-N-(2-pyridyl)amino]ethyl]-N-methyl-1,6-hexanediamine and the equimolar amounts of 1,1'-carbonyldiimidazole and 3-[3-(piperidinomethyl)phenoxy]propylamine as starting materials. Chromatographic working-up analogously to Example 63 yields the purified title compound in the form of a viscous oil; MS (+FAB method): m/z (rel. int. [%])=633 ([M+H]+, 1), 154 ([m-NO$_2$-benzylOH] 100); IR (KBr): 1640 cm$^{-1}$ (C=O). For further analysis, a portion of the compound is converted into the tartaric acid salt in an ethanol/ether solvent mixture; m.p.: 65°-69° C. (ethanol/ether).

EXAMPLE 72

N-[7-[N-[2-[N-(4-fluorobenzyl)-N-(2-pyridyl)amino]ethyl]-N-methylamino]heptyl]-N'-[3-[3-(piperidinomethyl)phenoxy]propyl]urea Preparation is effected analogously to Example 63, using 0.59 g (1.6 mmol) of N-[2-[N-(4-fluorobenzyl)-N-(2-pyridyl)amino]ethyl]-N-methyl-1,7-heptanediamine and the equimolar amounts of 1,1'-carbonyldiimidazole and 3-[3-(piperidinomethyl)phenoxy]propylamine as starting materials. Working up by chromatography analogously to Example 63 yields the purified title compound in the form of a viscous oil; MS (+FAB method): m/z (rel. int. [%])=647 ([M+H]+, 7), 229 (100); IR (KBr): 1634 cm$^{-1}$ (C=O). For further analysis, a portion of the compound is converted into the O,O'-ditoluoyltartaric acid salt and recrystallised from isopropanol/ether; m.p.: 112° C. (isopropanol/ether).

EXAMPLE 73

N-[3-[N-[2-[N-(4-fluorobenzyl)-N-(2-pyridyl)amino]ethyl]-N-methylamino]propyl]-N'-[4-[3-(piperidinomethyl)phenoxy]butyl]urea Preparation is effected analogously to Example 63, using 0.42 g (1.0 mmol) of N-[2-[N-(4-fluorobenzyl)-N-(2-pyridyl)amino]ethyl]-N-methyl-1,3-propanediamine and the equimolar amounts of 1,1'-carbonyldiimidazole and 4-[3-(piperidinomethyl)phenoxy]butylamine as starting materials. Working up by chromatography analogously to Example 63 yields the purified title compound in the form of a viscous oil; MS (+FAB method): m/z (rel. int. [%])=605 ([M+H]+, 14), 229 (100); IR (KBr): 1631 cm$^{-1}$ (C=O). For further analysis, a portion of the compound is converted into the O,O'-ditoluoyltartaric acid salt and recrystallised from isopropanol/ether; m.p.: 115° C. (isopropanol/ether).

EXAMPLE 74

N-[2-[N-[2-[N-(4-methoxybenzyl)-N-(2-pyridyl)amino]ethyl]-N-methylamino]ethyl]-N'-[3-[3-(piperidinomethyl)phenoxy]propyl]-2-nitro-1,1-ethenediamine Preparation is effected analogously to Example 22, using 0.85 g (2.7 mmol) of N-[2-[N-(4-methoxybenzyl)-N-(2-pyridyl)amino]ethyl]-N-methyl-1,2-ethanediamine and the equimolar amount of 1-methylthio-1-[3-[3-

(piperidinomethyl)phenoxy]propyl]amino-2-nitroethene as starting materials. Chromatographic working-up analogously to Example 22 yields the purified title compound in the form of a viscous oil; MS (+FAB method): m/z (rel. int. [%])=632 ([M+H]+, 8), 121 (100). For further analysis, a portion of the compound is converted into the tartaric acid salt and recrystallised from isopropanol/ether; m.p.: 102°-104° C. (isopropanol/ether).

EXAMPLE 75

N-[6-[N-[2-[N-(4-methoxybenzyl)-N-(2-pyridyl)amino]ethyl]-N-methylamino]hexyl]-N'-[3-[3-(piperidinomethyl)phenoxy]propyl]-2-nitro-1,1-ethenediamine Preparation is effected analogously to Example 22, using 0.54 g (1.45 mmol) of N-[2-[N-(4-methoxybenzyl)-N-(2-pyridyl)amino]ethyl]-N-methyl-1,6-hexanediamine and the equimolar amount of 1-methylthio-1-[3-[3-(piperidinomethyl)phenoxy]propyl]amino-2-nitroethene as starting materials. Working up by chromatography analogously to Example 22 yields the purified title compound in the form of a viscous oil; MS (+FAB method): m/z (rel. int. [%])=688 ([M+H]+, 5), 121 (100). For further analysis, a portion of the compound is converted into the tartaric acid salt in an ethanol/ether solvent mixture; m.p.: 73° C. (ethanol/ether).

EXAMPLE 76

N-cyano-N'-[2-[[(2-guanidino-4-thiazolyl)methyl]thio]ethyl]-N''-[2-[N-[2-[N-(4-methoxybenzyl)-N-(2-pyridyl)amino]ethyl]-N-methylamino]ethyl]guanidine Preparation is effected analogously to Example 1, using 0.53 g (1.7 mmol) of N-[2-[N-(4-methoxybenzyl)-N-(2-pyridyl)amino]ethyl]-N-methyl-1,2-ethanediamine and the equimolar amount of N-cyano-N'-[2-[[(2-guanidino-4-thiazolyl)methyl]thio]ethyl]-O-phenylisourea as starting materials. Working up by chromatography analogously to Example 1 yields the purified title compound in the form of a viscous oil which crystallises from absolute ether at −20° C. and is recrystallised from ethanol/ether; MS (+FAB method): m/z (rel. int. [%])=596 ([M+H]+, 1), 121 (100); IR (KBr): 2163 cm−1 (C≡N); m.p.: 56°-58° C. (ethanol/ether).

EXAMPLE 77

N-cyano-N'-[2-[[(2-guanidino-4-thiazolyl)methyl]thio]ethyl]-N''-[3-[N-[2-[N-(4-methoxybenzyl)-N-(2-pyridyl)amino]ethyl]-N-methylamino]propyl]guanidine Preparation is effected analogously to Example 1, using 0.52 g (1.6 mmol) of N-[2-[N-(4-methoxybenzyl)-N-(2-pyridyl)amino]ethyl]-N-methyl-1,3-propanediamine and the equimolar amount of N-cyano-N'-[2-[[(2-guanidino-4-thiazolyl)methyl]thio]ethyl]-O-phenylisourea as starting materials. Chromatographic working-up analogously to Example 1 yields the purified title compound in the form of a viscous oil that crystallises from ether at −20° C.; MS (+FAB method): m/z (rel. int. [%])=610 ([M+H]+, 1), 121 (100); IR (KBr): 2161 cm−1 (C≡N); m.p.: 54° C. (ether).

EXAMPLE 78

N-cyano-N'-[2-[[(2-guanidino-4-thiazolyl)methyl]thio]ethyl]-N''-[4-[N-[2-[N-(4-methoxybenzyl)-N-(2-pyridyl)amino]ethyl]-N-methylamino]butyl]guanidine Preparation is effected analogously to Example 1, using 0.54 g (1.6 mol) of N-[2-[N-(4-methoxybenzyl)-N-(2-pyridyl)amino]ethyl]-N-methyl-1,4-butanediamine and the equimolar amount of N-cyano-N'-[2-[[(2-guanidino-4-thiazolyl)methyl]thio]ethyl]-O-phenylisourea as starting materials. Working up by chromatography analogously to Example 1 yields the purified title compound in the form of a dry foam. MS (+FAB method): m/z (rel. int. [%])=624 ([M+H]+, 1), 121 (100) IR (KBr): 2163 cm−1 (C≡N).

EXAMPLE 79

N-cyano-N'-[2-[[(2-guanidino-4-thiazolyl)methyl]thio]ethyl]-N''-[6-[N-[2-[N-(4-methoxybenzyl)-N-(2-pyridyl)amino]ethyl]-N-methylamino]hexyl]-guanidine Preparation is effected analogously to Example 1, using 0.57 g (1.5 mmol) of N-[2-[N-(4-methoxybenzyl)-N-(2-pyridyl)amino]ethyl]-N-methyl-1,6-hexanediamine and the equimolar amount of N-cyano-N'-[2-[[(2-guanidino-4-thiazolyl)methyl]thio]ethyl]-O-phenylisourea as starting materials. Working up by chromatography analogously to Example 1 yields the purified title compound in the form of a viscous oil that crystallises from ether at −20° C.; MS (+FAB method): m/z (rel. int. [%])=652 ([M+H]+, 12), 121 (100); IR (KBr): 2162 cm−1 (C≡N); m.p.: 52° C. (ether).

EXAMPLE 80

N-cyano-N'-[2-[N-[2-[N-(4-fluorobenzyl)-N-(2-pyridyl)amino]ethyl]-N-methylamino]ethyl]-N''-[2-[[(2-guanidino-4-thiazolyl)methyl]thio]ethyl]guanidine Preparation is effected analogously to Example 1, using 0.30 g (1.0 mmol) of N-[2-[N-(4-fluorobenzyl)-N-(2-pyridyl)amino]ethyl]-N-methyl-1,2-ethanediamine and the equimolar amount of N-cyano-N'-[2-[[(2-guanidino-4-thiazolyl)methyl]thio]ethyl]-O-phenylisourea as starting materials. Working up by chromatography analogously to Example 1 yields the purified title compound in the form of a viscous oil; MS (+FAB method): m/z (rel. int. [%])=584 ([M+H]+, 3), 109 (100); IR (KBr): 2165 cm−1 (C≡N). For further analysis, a portion of the compound is converted into the tartaric acid salt and recrystalised from isopropanol/ether; m.p.: 109° C. (isopropanol/ether).

EXAMPLE 81

N-cyano-N'-[3-[N-[2-[N-(4-fluorobenzyl)-N-(2-pyridyl)amino]ethyl]-N-methylamino]propyl]-N''-[2-[[(2-guanidino-4-thiazolyl)methyl]thio]ethyl]guanidine Preparation is effected analogously to Example 1, using 0.53 g (1.67 mmol) of N-[2-[N-(4-fluorobenzyl)-N-(2-pyridyl)amino]ethyl]-N-methyl-1,3-propanediamine and the equimolar amount of N-cyano-N'-[2-[[(2-guanidino-4-thiazolyl)methyl]thio]ethyl]-O-phenylisourea as starting materials. Working up by chromatography analogously to Example 1 yields the purified title compound in the form of a viscous oil. MS (+FAB method): m/z (rel. int. [%])=598 ([M+H]+, 6), 109 (100); IR (KBr): 2163 cm−1 (C≡N); $C_{27}H_{36}FN_{11}S_2$ (597.80).

EXAMPLE 82

N-cyano-N'-[4-[N-[2-[N-(4-fluorobenzyl)-N-(2-pyridyl)amino]ethyl]-N-methylamino]butyl]-N''-[2-[[(2-guanidino-4-thiazolyl)methyl]thio]ethyl]guanidine Preparation is effected analogously to Example 1, using 0.33 g (1.0 mmol) of N-[2-[N-(4-fluorobenzyl)-N-

(2-pyridyl)amino]ethyl]-N-methyl-1,4-butanediamine and the equimolar amount of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a viscous oil; MS (+FAB method): m/z (rel. int. [%])=612 ([M+H]+, 49), 229 (100); IR (KBr): 2165 cm$^{-1}$ (C≡N). For further analysis, a portion of the compound is converted into the O,O'-ditoluoyltartaric acid salt in an ethanol/ether solvent mixture; m.p.: 137° C. (ethanol/ether).

EXAMPLE 83

N-cyano-N'-[5-[N-[2-[N-(4-fluorobenzyl)-N-(2-pyridyl)amino]ethyl]-N-methylamino]pentyl]-N''-[2-[[(2-guanidino-4-thiazolyl)methyl]thio]ethyl]guanidine Preparation is effected analogously to Example 1, using 0.51 g (1.5 mmol) of N-[2-[N-(4-fluorobenzyl)-N-(2-pyridyl)amino]ethyl]-N-methyl-1,5-pentanediamine and the equimolar amount of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a viscous oil; MS (+FAB method): m/z (rel. int. [%])=626 ([M+H]+, 3), 154 ([m-NO$_2$benzylOH] 100); IR (KBr): 2162 cm$^-$(C≡N). For further analysis, a portion of the compound is converted into the tartaric acid salt and recrystallised from isopropanol/petroleum ether; m.p.: 103° C. (isopropanol/petroleum ether).

EXAMPLE 84

N-cyano-N'-[6-[N-[2-[N-(4-fluorobenzyl)-N-2-pyridyl)amino]ethyl]-N-methylamino]hexyl]-N''-[2-[[(2-guanidino-4-thiazolyl)methyl]thio]ethyl]guanidine Preparation is effected analogously to Example 1, using 0.50 g (1.4 mmol) of N-[2-[N-(4-fluorobenzyl)-N-(2-pyridyl)amino]ethyl]-N-methyl-1,6-hexanediamine and the equimolar amount of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a viscous oil; MS (+FAB method): m/z (rel. int. [%])=639 ([M+H]+, 9), 229 (100); IR (KBr): 2162 cm$^{-1}$ (C≡N). For further analysis, a portion of the compound is converted into the tartaric acid salt in an ethanol/ether solvent mixture; m.p.: 75° C. (ethanol/ether).

EXAMPLE 85

N-cyano-N'-[7-[N-[2-[N-(4-fluorobenzyl)-N-(2-pyridyl)amino]ethyl]-N-methylamino]heptyl]-N'''-[2-[[(2-guanidino-4-thiazolyl)methyl]thio]ethyl]guanidine Preparation is effected analogously to Example 1, using 0.57 g (1.53 mmol) of N-[2-[N-(4-fluorobenzyl)-N-(2-pyridyl)amino]ethyl]-N-methyl-1,7-heptanediamine and the equimolar amount of N-cyano-N'-[2-[[(2-guanidino-4-thiazolyl)methyl]thio]ethyl]-O-phenyl-isourea as starting materials. Working up by chromatography analogously to Example 1 yields the purified title compound in the form of a viscous oil; MS (+FAB method): m/z (rel. int. [%])=654 ([M+H]+, 2), 91 (100); IR (KBr): 2163 cm$^{-1}$ (C≡N). For further analysis, a portion of the compound is converted into the O,O'-ditoluoyltartaric acid salt in an ethanol/ether solvent mixture; m.p. 118° C. (ethanol/ether).

EXAMPLE 86

N-[2-[[(2-guanidino-4-thiazolyl)methyl]thio]ethyl]-N'-[2-[N-2-[N-(4-methoxybenzyl)-N-(2-pyridyl)amino]ethyl]-N-methylamino]ethyl]urea Preparation is effected analogously to Example 63, using 0.53 g (1.7 mmol) of N-[2-[N-(4-methoxybenzyl)-N-(2-pyridyl)amino]ethyl]-N-methyl-1,2-ethanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=572 ([M+H]+, 1), 121 (100); IR (KBr): 1644 cm$^{-1}$ (C=O). For further analysis, a portion of the compound is converted into the picric acid salt and recrystallised from ethanol; m.p.: 84° C. (ethanol).

EXAMPLE 87

N-[2-[[(2-guanidino-4-thiazolyl)methyl]thio]ethyl]-N'-[3-[N-[2-[N-(4-methoxybenzyl)-N-(2-pyridyl)amino]ethyl]-N-methylamino]propyl]urea Preparation is effected analogously to Example 63, using 1.00 g (3.0 mmol) of N-[2-[N-(4-methoxybenzyl)-N-(2-pyridyl)amino]ethyl]-N-methyl-1,3-propanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=586 ([M+H]+, 4), 121 (100); IR (KBr): 1717 cm$^{-1}$ (C=O). For further analysis, a portion of the compound is converted into the picric acid salt and recrystallised from ethanol; m.p.: 106°-109° C. (ethanol).

EXAMPLE 88

N-[2-[[(2-guanidino-4-thiazolyl)methyl]thio]ethyl]-N'-[4-[N-[2-[N-(4-methoxybenzyl)-N-(2-pyridyl)amino]ethyl]-N-methylamino]butyl]urea Preparation is effected analogously to Example 63, using 0.54 g (1.58 mmol) of N-[2-[N-(4-methoxybenzyl)-N-(2-pyridyl)amino]ethyl]-N-methyl-1,4-butanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=600 ([M+H]+, 1), 121 (100); IR (KBr): 1599 cm$^{-1}$ (C=O). For further analysis, a portion of the compound is converted into the picric acid salt and recrystallised from ethanol; m.p.: 104°-106° C. (ethanol).

EXAMPLE 89

N-[2-[[(2-guanidino-4-thiazolyl)methyl]thio]ethyl]-N'-[6-[N-[2-[N-(4-methoxybenzyl)-N-(2-pyridyl)amino]ethyl]-N-methylamino]hexyl]urea Preparation is effected analogously to Example 63, using 0.74 g (2.0 mmol) of N-[2-[N-(4-methoxybenzyl)-N-(2-pyridyl)amino]ethyl]-N-methyl-1,6-hexanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=628 ([M+H]+, 4), 121 (100); IR (KBr): 1597 cm$^{-1}$ (C=O). For further analysis, a portion of the compound is converted into the tartaric acid salt in an ethanol/ether solvent mixture; m.p.: 60° C. (ethanol/ether).

EXAMPLE 90

N-[2-[N-[2-[N-(4-fluorobenzyl)-N-(2-pyridyl)amino]ethyl]-N-methylamino]ethyl]-N'-[2-[[(2-guanidino-4-thiazolyl)methyl]thio]ethyl]urea Preparation is effected analogously to Example 63, using 0.29 g (0.97 mmol) of N-[2-[N-(4-fluorobenzyl)-N-(2-pyridyl)amino]ethyl]-N-methyl-1,2-ethanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil: MS (+FAB method): m/z (rel. int. [%])=560 ([M+H]+, 8), 78 (100); IR (KBr): 1659 cm$^{-1}$ (C=O). For further analysis, a portion of the compound is converted into the O,O'-ditoluoyltartaric acid salt in an ethanol/ether solvent mixture; m.p.: 132° C. (ethanol/ether).

EXAMPLE 91

N-[3-[N-[2-[N-(4-fluorobenzyl)-N-(2-pyridyl)amino]ethyl]-N-methylamino]propyl]-N'-[2-[[(2-guanidino-4-thiazolyl)methyl]thio]ethyl]urea Preparation is effected analogously to Example 63, using 0.33 g (1.05 mmol) of N-[2-[N-(4-fluorobenzyl)-N-(2-pyridyl)amino]ethyl]-N-methyl-1,3-propanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a dry foam. MS (+FAB method): m/z (rel. int. [%])=574 ([M+H]+, 9), 109 (100) IR (KBr): 1682 cm$^{-1}$ (C=O).

EXAMPLE 92

N-[4-[N-[2-[N-(4-fluorobenzyl)-N-(2-pyridyl)amino]ethyl]-N-methylamino]butyl]-N'-[2-[[(2-guanidino-4-thiazolyl)methyl]thio]ethyl]urea Preparation is effected analogously to Example 63, using 0.20 g (0.6 mmol) of N-[2-[N-(4-fluorobenzyl)-N-(2-pyridyl)amino]ethyl]-N-methyl-1,4-butanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil. MS (+FAB method): m/z (rel. int. [%])=588 ([M+H]+, 2), 109 (100); IR (KBr): 1685 cm$^{-1}$ (C=O); $C_{27}H_{38}FN_9OS_2$ (587.90).

EXAMPLE 93

N-[5-[N-[2-(4-fluorobenzyl)-N-(2-pyridyl)amino]ethyl]-N-methylamino]pentyl]-N'-[2-[[(2-guanidino-4-thiazolyl)methyl]thio]ethyl]urea Preparation is effected analogously to Example 63, using 0.51 g (1.5 mmol) of N-[2-[N-(4-fluorobenzyl)-N-(2-pyridyl)amino]ethyl]-N-methyl-1,5-pentanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=602 ([M+H]+, 3), 77 (100); IR (KBr): 1687 cm$^{-1}$ (C=O). For further analysis, a portion of the compound is converted into the tartaric acid salt and recrystallised from isopropanol/ether; m.p.: 91°-93° C. (isopropanol/ether).

EXAMPLE 94

N-[6-[N-[2-[N-(4-fluorobenzyl)-N-(2-pyridyl)amino]ethyl]-N-methylamino]hexyl]-N'-[2-[[(2-guanidino-4-thiazolyl)methyl]thio]ethyl]urea Preparation is effected analogously to Example 63, using 0.50 g (1.4 mmol) of N-[2-[N-(4-fluorobenzyl)-N-(2-pyridyl)amino]ethyl]-N-methyl-1,6-hexanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=616 ([M+H]+, 12), 229 (100); IR (KBr): 1640 cm$^{-1}$ (C=O). For further analysis, a portion of the compound is converted into the tartaric acid salt in an ethanol/ether solvent mixture; m.p.: 95° C. (ethanol/ether).

EXAMPLE 95

N-[7-[N-[2-[N-(4-fluorobenzyl)-N-(2-pyridyl)amino]ethyl]-N-methylamino]heptyl]-N'-[2-[[(2-guanidino-4-thiazolyl)methyl]thio]ethyl]urea Preparation is effected analogously to Example 63, using 0.59 g (1.6 mmol) of N-[2-[N-(4-fluorobenzyl)-N-(2-pyridyl)amino]ethyl]-N-methyl-1,7-heptanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=630 ([M+H]+, 3), 109 (100); IR (KBr): 1666 cm$^{-1}$ (C=O). For further analysis, a portion of the compound is converted into the O,O'-ditoluoyltartaric acid salt and recrystallised from isopropanol/ether; m.p.: 125° C. (isopropanol/ether).

EXAMPLE 96

N-[2-[[(2-guanidino-4-thiazolyl)methyl]thio]ethyl]-N'-[6-[N-[2-[N-(4-methoxybenzyl)-N-(2-pyridyl)amino]ethyl]-N-methylamino]hexyl]-2-nitro-1,1-ethenediamine Preparation is effected analogously to Example 22, using 0.41 g (1.8 mmol) of 2-[[(2-guanidino-4-thiazolyl)methyl]thio]ethaneamine and the equimolar amount of 1-[6-[N-[2-[N-(4-methoxybenzyl)-N-(2-pyridyl)amino]ethyl]-N-methylamino]hexyl]amino-1-methylthio-2-nitro-ethene. Working up by chromatography analogously to Example 22 yields the purified title compound in the form of a viscous oil; MS (+FAB method): m/z (rel. int. [%])=671 ([M+H]+, 1), 121 (100). For further analysis, a portion of the compound is converted into the tartaric acid salt in an ethanol/ether solvent mixture; m.p.: 60° C. (ethanol/ether).

The starting material is prepared as follows:
N-(4-methoxybenzyl)-N'-methyl-N-(2-pyridyl)-1,2-ethanediamine is reacted with the equimolar amount of 6-bromohexanonitrile and three times the molar amount of $Na_2CO_3$ in 60 ml of anhydrous acetonitrile while heating under reflux for 3 hours. The reaction batch is cooled to room temperature and water is added until the precipitate has dissolved. The batch is extracted with toluene. The combined organic phases are dried with MgSO₄ and the toluene is distilled off in vacuo to yield N-[2-[N-(4-methoxybenzyl)-N-(2-pyridyl)amino]ethyl]-N-methyl-6-aminohexanonitrile in the form of a brownish oil. The oil is dissolved in 20 ml of absolute THF and, while cooling with ice and stirring, is introduced slowly into a suspension of twice the molar amount of LiAlH₄ in 50 ml of absolute ether. The batch is stirred for 30 minutes and then, while cooling with ice, is hydrolysed with water-saturated ether and the dropwise addition of a small amount of 10% sodium hydroxide solution until the exothermic reaction has ceased and a white precipitate forms. The batch is stirred for a further 30 minutes and then suction-filtered and the precipitate is washed several times with ether. The filtrate is washed with water, dried over Na₂SO₄ and concentrated to dryness in vacuo. The resulting crude product is purified by thick-layer chromatography, using methylene chloride containing 1% (V/V) methanol as eluant, to yield N-[2-[N-(4-methoxybenzyl)-N-(2-pyridyl)amino]ethyl]-N-methyl-1,6-hexanediamine of sufficient purity for the subsequent reaction. 0.43 g (1.16 mmol) of that amine is heated under reflux for 4 hours with 0.19 g (1.16 mmol) of 1,1-dimethylthio-2-nitroethene [R. Gomper, H. Schäfer, Chem. Ber. 100. 599 (1967)] in 20 ml of absolute acetonitrile. When the reaction is complete (TLC monitoring: chloroform/methanol 95/5 V/V), the solvent is distilled off in vacuo. The resulting product, 1-[6-[N-[2-[N-(4-methoxybenzyl)-N-(2-pyridyl)amino]ethyl]-N-methylamino]hexyl]amino-1-methylthio-2-nitroethene, is sufficiently pure for the subsequent reaction.

EXAMPLE 97

N-[4-[N-[2-(diphenylmethoxy)ethyl]-N-methylamino]butyl]-N'-[2-[[(2-guanidino-4-thiazolyl)methyl]thio]ethyl]urea Preparation is effected analogously to Example 63, using 0.37 g (1.2 mmol) of N-[2-(diphenylmethoxy)ethyl]-N-methyl-1,4-butanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=570 ([M+H]+, 11), 167 (100); IR (KBr): 1644 cm⁻¹ (C=O). For further analysis, a portion of the compound is converted into the tartaric acid salt and recrystallised from acetonitrile/isopropanol/petroleum ether; m.p.: 101° C. (acetonitrile/isopropanol/petroleum ether).

EXAMPLE 98

N-[4-[N-(3',3'-diphenylpropyl)-N-methylamino]butyl]-N'-[2-[[(2-guanidino-4-thiazolyl)methyl]thio]ethyl]urea Preparation is effected analogously to Example 63, using 0.53 g (1.8 mmol) of N-(3',3'-diphenylpropyl)-N-methyl-1,4-butanediamine and the equimolar amounts of 1,1'-carbonyldiimidazole and 2-[[(2-guanidino-4-thiazolyl)methyl]thio]ethaneamine as starting materials. Working up by chromatography analogously to Example 63 yields the purified title compound in the form of a viscous oil; MS (+FAB method): m/z (rel. int. [%])=554 ([M+H]+, 2), 91 (100); IR (KBr): 1643 cm⁻¹ (C=O). For further analysis, a portion of the compound is converted into the O,O'-ditoluoyltartaric acid salt in an ethanol/ether solvent mixture; m.p.: 136° C. (ethanol/ether).

EXAMPLE 99

N-[2-[[(2-guanidino-4-thiazolyl)methyl]thio]ethyl]-N'-[6-[N-[2-[N-(4-methoxybenzyl)-N-(2-pyridyl)amino]ethyl]-N-methylamino]hexyl]thiourea 0.48 g (1.3 mmol) of N-[2-[N-(4-methoxybenzyl)-N-(2-pyridyl)amino]ethyl]-N-methyl-1,6-hexanediamine and 0.27 g (1.3 mmol) of dicyclohexylcarbodiimide are dissolved at −10° C. in absolute ether with 0.5 ml of carbon disulfide, the temperature is increased in the course of 3 hours to 20° C. and the batch is stirred for a further 12 hours. The solid that precipitates is filtered off and the filtrate is concentrated in vacuo. 0.30 g (1.3 mmol) of 2-[[(2-guanidino-4-thiazolyl)methyl]thio]ethaneamine dissolved in a small amount of absolute ethanol is added to the concentrated residue and the reaction batch is heated under reflux for 2 hours. It is then concentrated in vacuo and the residue is purified by rotation chromatography to yield the purified title compound in the form of a viscous oil; MS (+FAB method): m/z (rel. int. [%])=644 ([M+H]+, 1), 121 (100). For further analysis, a portion of the compound is converted into the tartaric acid salt and recrystallised from acetonitrile/isopropanol/petroleum ether; m.p.: 78° C. (acetonitrile/isopropanol/petroleum ether).

EXAMPLE 100

N-cyano-N'-[2-[[5-[(dimethylamino)methyl]furfuryl]thio]ethyl]-N''-[3-[N-[2-[N-(4-methoxybenzyl)-N-(2-pyridyl)amino]ethyl]-N-methylamino]propyl]guanidine Preparation is effected analogously to Example 1, using 0.55 g (1.6 mmol) of N-[2-[N-(4-methoxybenzyl)-N-(2-pyridyl)amino]ethyl]-N-methyl-1,3-propanediamine and the equimolar amount of N-cyano-N'-[2-[[5-[(dimethylamino)methyl]furfuryl]thio]ethyl]-O-phenylisourea. Working up by chromatography analogously to Example 1 yields the purified title compound in the form of a viscous oil; MS (+FAB method): m/z (rel. int. [%])=593 ([M+H]+, 4), 121 (100); IR (KBr): 2163 cm⁻¹ (C≡N). For further analysis, a portion of the compound is converted into the tartaric acid salt and recrystallised from isopropanol/ether; m.p.: 74° C. (isopropanol/ether).

The starting material is prepared as follows:

While stirring, the equimolar amount of 2-[[5-[(dimethylamino)methyl]furfuryl]thio]ethaneamine [J. Bradshaw et al., Br. J. Pharmacol. 66, 464P (1979)] is added to a suspension of approx. 0.1 mol of N-cyanodiphenylimidocarbonate in 100 ml of diethyl ether. After approx. 15 minutes' stirring, the product, N-cyano-N'-[2-[[5-[(dimethylamino)methyl]furfuryl]thio]ethyl]-O-phenyl-isourea, precipitates copiously, or it crystallises after concentration of the solution. The product is suction-filtered, washed with diethyl ether and dried.

EXAMPLE 101

N-[2-[[5-[(dimethylamino)methyl]furfuryl]thio]ethyl]-N'-[2-[N-[2-[N-(4-fluorobenzyl)-N-(2-pyridyl)amino]ethyl]-N-methylamino]ethyl]urea Preparation is effected analogously to Example 63, using 0.56 g (1.8 mmol) of N-[2-[N-(4-fluorobenzyl)-N-(2-pyridyl)amino]ethyl]-N-methyl-1,2-ethanediamine and the equimolar amounts of 1,1'-carbonyldiimidazole and 2-[[5-[(dimethylamino)methyl]-furfuryl]thio]ethylamine as starting materials. Working up by chromatography analogously to Example 1 yields the purified title compound in the form of a viscous oil; MS(+FAB method): m/z (rel. int. [%])=543 ([M+H]+, 14), 109 (100); IR (KBr): 1641 cm$^{-1}$ (C=O). For further analysis, a portion of the compound is converted into the O,O'-ditoluoyltartaric acid salt and recrystallised from isopropanol/ether; m.p.: 90° C. (isopropanol/ether).

EXAMPLE 102

N-[2-[[5-[(dimethylamino)methyl]furfuryl]thio]ethyl]-N'-[3-[N-[2-[N-(4-fluorobenzyl)-N-(2-pyridyl)amino]ethyl]-N-methylamino]propyl]urea Preparation is effected analogously to Example 63, using 0.57 g (1.8 mmol) of N-[2-[N-(4-fluorobenzyl)-N-(2-pyridyl)amino]ethyl]-N-methyl-1,3-propanediamine and the equimolar amounts of 1,1'-carbonyldiimidazole and 2-[[5-[(dimethylamino)methyl]furfuryl]thio]ethylamine as starting materials. Working up by chromatography analogously to Example 1 yields the purified title compound in the form of a viscous oil; MS(+FAB method): m/z (rel. int. [%])=557 ([M+H]+, 1), 109 (100); IR (KBr): 1600 cm$^{-1}$ (C=O). For further analysis, a portion of the compound is converted into the O,O'-ditoluoyltartaric acid salt in an ethanol/ether solvent mixture; m.p.: 102° C. (ethanol/ether).

EXAMPLE 103

N-[2-[[5-[(dimethylamino)methyl]furfuryl]thio]ethyl]-N'-[4-[N-[2-[N-(4-fluorobenzyl)-N-(2-pyridyl)amino]ethyl]-N-methylamino]butyl]urea Preparation is effected analagously to Example 63, using 0.50 g (1.5 mmol) of N-[2-[N-(4-fluorobenzyl)-N-(2-pyridyl)amino]ethyl]-N-methyl-1,4-butanediamine and the equimolar amounts of 1,1'-carbonyldiimidazole and 2-[[5-[(dimethylamino)methyl]furfuryl]thio]ethylamine as starting materials. Working up by chromatography analogously to Example 1 yields the purified title compound in the form of a viscous oil; MS (+FAB method): m/z (rel. int. [%])=571 ([M+H]+, 109 (100); IR (KBr): 1640 cm$^{-1}$ (C=O). For further analysis, a portion of the compound is converted into the tartaric acid salt in an ethanol/ether solvent mixture; m.p.: 74° C. (ethanol/ether).

EXAMPLE 104

N-[2-[[5-[(dimethylamino)methyl]furfuryl]thio]ethyl]-N'-[3-[N-[2-[N-(4-fluorobenzyl)-N-(2-pyridyl)amino]ethyl]-N-methylamino]propyl]-2-nitro-1,1-ethenediamine Preparation is effected analogously to Example 22, using 0.54 g (1.7 mmol) of N-[2-[N-(4-fluorobenzyl)-N-(2-pyridyl)amino]ethyl]-N-methyl-1,3-propanediamine and the equimolar amount of 1-[2-[[5-[(dimethylamino)methyl]furfuryl]thio]ethyl]amino-1-methylthio-2-nitroethane as starting materials. Working up by chromatography analogously to Example 22 yields the purified title compound in the form of a viscous oil; MS (+FAB method): m/z (rel. int. [%])=600 ([M+H]+, 12), 109 (100). For further analysis, a portion of the compound is converted into the tartaric acid salt in an ethanol/ether solvent mixture; m.p.: 63° C. (ethanol/ether).

EXAMPLE 105

N-[2-[[(2-guanidino-4-thiazolyl)methyl]thio]ethyl]-N'-[6-[N-methyl-N-[2-[1-(2-pyridyl)ethyl]inden-2-yl]ethylamino]hexyl]-2-nitro-1,1-ethenediamine Preparation is effected analogously to Example 22, using 0.60 g (2.6 mmol) of 2-[[(2-guanidino-4-thiazolyl)methyl]thio]ethaneamine and the equimolar amount of 1-[[6-[N-methyl-N-[[2-[1-(2-pyridyl)ethyl]inden-2-yl]ethyl]amino]hexyl]amino-1-methylthio-2-nitro-ethene as starting materials. Working up by chromatography analogously to Example 22 yields the purified title compound in the form of a dry foam; MS (+FAB method): m/z (rel. int. [%])=678 ([M+H]+, 11), 93 (100).

The starting material is prepared as follows:

4.0 g (9.8 mmol) of dimethindene maleate are dissolved in water. The solution is rendered alkaline with 2N sodium hydroxide solution and extracted by shaking four times with n-hexane. The combined organic phases are dried with Na$_2$SO$_4$ and the solvent is distilled off in vacuo. The free base is dissolved in 10 ml of absolute 1,2-dichloroethane and a spatula tip of Na$_2$CO$_3$ (anhydrous) is added to that solution. The mixture is cooled to 0° C. and at that temperature 2.79 g (19.6 mmol) of α-chloroethylchloroformate are added dropwise. The batch is then heated under reflux for 12 hours. After cooling, excess Na$_2$CO$_3$ is filtered off and the solvent is distilled off in vacuo. The oily residue is heated under reflux overnight in methanol, CO$_2$ being evolved. The methanol is finally distilled off in vacuo to yield 2.7 g of N-methyl-2-[3-[1-[-(2-pyridyl)ethyl]inden-2-yl]ethaneamine [S. Radler, Dissertation, Westfälische Wilhelms-Universität Münster (1989] in the form of the hydrochloride, which is a colourless oil, which is reacted using 6-bromohexanonitrile and by subsequent treatment with LiAlH$_4$ analogously to the process indicated in Example 96 to form N-methyl-N-[2-[3-[1-(2-pyridyl)ethyl]inden-2-yl]ethyl]-1,6-hexanediamine and then (by reaction with 1,1-dimethylthio-2-nitroethene) 1-[[6-[N-methyl-N-[[2-[1-(2-pyridyl)ethyl]inden-2-yl]ethyl]amino]hexyl]amino-1-methylthio-2-nitro-ethene.

EXAMPLE 106

N-[7-[N-[3-(4-chlorophenyl)-3-(2-pyridyl)propyl]-N-methylamino]heptyl]-N'-[3-[3-(piperidinomethyl)phenoxy]propyl]-2-nitro-1,1-ethenediamine A mixture of 0.73 g (1.9 mmol) of N-[3-(4-chlorophenyl)-3-(2-pyridyl)propyl]-N-methyl-1,7-heptanediamine and an equimolar amount of 1-methylthio-1-[3-[3-(piperidinomethyl)phenoxy]propyl]amino-2-nitroethene is heated under reflux for 12 hours in 20 ml of acetonitrile. The batch is then freed of solvent and the title compound is isolated in the form of a viscous oil by means of preparative thick-layer chromatography (eluant: ethyl acetate/methanol 9+1, ammonia atmosphere); MS (+FAB method): m/z (rel. int. [%])=691 ([M+H]$^{30}$ 12), 230 (100).

EXAMPLE 107

An ointment comprising 0.05 percent by weight active ingredient, for example N-[3-[N-[3-(4-chlorophenyl)-3-(2-pyridyl)propyl]-N-methylamino]propyl]-N'-[3-[3-(piperidinomethyl)-phenoxy]propyl]urea, is prepared as follows:

| Composition | Percent by weight |
| --- | --- |
| active ingredient | 0.05 |
| vaseline | 45.00 |
| paraffin oil | 19.60 |
| cetyl alcohol | 5.00 |
| beeswax | 5.00 |
| sorbitan sesquioleate | 5.00 |
| p-hydroxybenzoate | 0.20 |
| water, demineralised | 20.15 |

The fatty substances and emulsifiers are melted together. The preservative is dissolved in water and the solution is incorporated into the fatty melt at elevated temperature by emulsification. After cooling, a suspension of the active ingredient in a portion of the fatty melt is incorporated into the emulsion.

EXAMPLE 108

Tablets, each comprising 50 mg of active ingredient, for example N-[7-[N-[3-(4-chlorophenyl)-3-(2-pyridyl)propyl]-N-methylamino]heptyl]-N'-[2-[[2-guanidino-4-thiazolyl)-methyl]thio]ethyl]urea, are prepared as follows:

| Composition (10000 tablets) | |
| --- | --- |
| active ingredient | 500.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of the potato starch and the mixture is moistened with an ethanolic solution of the gelatin and granulated through a seive. After drying, the remainder of the potato starch, the magnesium stearate, the talc and the silica are added and the mixture is compressed to form tablets each weighing 145 mg and comprising 50 mg of active ingredient, which may, if desired, be provided with breaking notches for finer adaptation of the dose.

What is claimed is:

1. An arylalkylamine derivative of the formula (I)

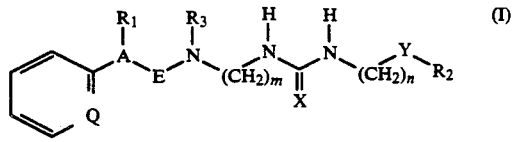

wherein
$R_1$ is phenyl which is unsubstituted or mono- or di-substituted by at least one member selected from the group consisting of halogen, $C_1$–$C_3$ alkyl and $C_1$–$C_3$ alkoxy,
A is CH,
E is —$(CH_2)_p$—, —O—$(CH_2)_p$— or —S—$(CH_2)_p$— wherein p is 2, 3 or 4,
Q is a nitrogen atom,
$R_2$ is a member selected from the group consisting of piperidino-$C_1$–$C_3$ alkyl-phenyl, guanidine-thiazolyl-$C_1$–$C_3$ alkyl and (N,N-di-$C_1$–$C_3$ alkylamino-$C_1$–$C_3$ alkyl)-furanyl-$C_1$–$C_3$ alkyl,
$R_3$ is hydrogen or $C_1$–$C_3$ alkyl,
X is oxygen or sulfur,
m is 2, 3, 4, 5, 6, 7 or 8,
n is 1, 2, 3 or 4, and
Y is sulfur or oxygen,
or a stereoisomeric form, a hydrate or a physiologically acceptable said thereof.

2. An arylalkylamine derivative according to claim 1 wherein p is 2 or 3.

3. An arylalkylamine derivative according to claim 1 wherein $R_1$ is phenyl which is unsubstituted or is substituted by halogen or $C_1$–$C_3$ alkyl, p is 2, $R_2$ is a member selected from the group consisting of 3-piperidinomethyl-phenyl, 2-guanidino-thiazol-4-yl methyl and 5-(N,N-dimethylaminomethyl)-furan-2-yl methyl, $R_3$ is $C_1$–$C_3$ alkyl and n is 2, 3 or 4.

4. An arylalkylamine derivative according to claim 1 wherein $R_2$ is 2-guanidino-thiazol-4-yl methyl.

5. An arylalkylamine derivative according to claim 1 wherein $R_2$ is 5-(N,N-dimethylaminomethyl)-furan-2-yl methyl.

6. An arylalkylamine derivative according to claim 1 wherein $R_2$ is 3-piperidinomethyl-phenyl.

7. N-[7-[N-[3-(4-chlorophenyl)-3-(2-pyridyl)propyl]-N-methylamino]heptyl]-N'-[2-[[(2-guanidino-4thiazolyl)methyl]thio]ethyl]urea according to claim 1 or a pharmaceutically acceptable salt thereof.

8. A pharmaceutical composition for the treatment of disorders that respond to the inhibition of histamine $H_1$- and $H_2$-receptors comprising a therapeutically effective amount of a compound according to claim 1 and at least one pharmaceutically acceptable carrier therefor.

9. A pharmaceutical composition according to claim 8 comprising N-[7-[N-[3-(4-chlorophenyl)-3-(2-pyridyl)propyl]-N-methylamino]heptyl]-N'-[2-[[(2-guanidino-4-thiazolyl)methyl]thio]ethyl]urea or a pharmaceutically acceptable salt thereof.

10. A method for the treatment of disorders that respond to the inhibition of histamine $H_1$- and $H_2$-receptors, which comprises administering to a mammal in need thereof a therapeutically effective amount of a compound according to claim 1.

* * * * *